(12) United States Patent
Locke et al.

(10) Patent No.: US 11,446,049 B2
(45) Date of Patent: Sep. 20, 2022

(54) WOUND CLEANING TOOL WITH FLUID DELIVERY AND REMOVAL CAPABILITIES

(71) Applicant: KCI Licensing, Inc., San Antonio, TX (US)

(72) Inventors: Christopher Brian Locke, Bournemouth (GB); Benjamin Andrew Pratt, Poole (GB); Thomas Alan Edwards, Hampshire (GB)

(73) Assignee: KCl Licensing, Inc., San Antonio, TX (US)

( * ) Notice: Subject to any disclaimer, the term of this patent is extended or adjusted under 35 U.S.C. 154(b) by 469 days.

(21) Appl. No.: 16/631,794

(22) PCT Filed: Jul. 11, 2018

(86) PCT No.: PCT/US2018/041663
§ 371 (c)(1),
(2) Date: Jan. 16, 2020

(87) PCT Pub. No.: WO2019/027644
PCT Pub. Date: Feb. 7, 2019

(65) Prior Publication Data
US 2020/0205848 A1     Jul. 2, 2020

Related U.S. Application Data

(60) Provisional application No. 62/539,366, filed on Jul. 31, 2017.

(51) Int. Cl.
*A61B 17/32* (2006.01)
*A61B 17/00* (2006.01)

(52) U.S. Cl.
CPC .... *A61B 17/32* (2013.01); *A61B 2017/00199* (2013.01); *A61B 2017/00221* (2013.01);
(Continued)

(58) Field of Classification Search
CPC .................. A61B 17/32; A61B 2017/00199
See application file for complete search history.

(56) References Cited

U.S. PATENT DOCUMENTS

| 1,355,846 A | 10/1920 | Rannells |
|---|---|---|
| 2,547,758 A | 4/1951 | Keeling |

(Continued)

FOREIGN PATENT DOCUMENTS

| AU | 550575 B2 | 3/1986 |
|---|---|---|
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Christian A Sevilla

(57) ABSTRACT

A treatment system (100) for debriding an area of a tissue site is disclosed. In some embodiments, the system may include a debridement tool (122) which may be fluidly connected to a negative-pressure source (116) and a fluid source (118). The system may also include a control unit for interfacing with an operator and for regulating the application of negative pressure and delivery of treatment fluid to the debridement tool. The debridement tool may include multiple fluid conduits for delivering and removing fluid to and from the tissue site, as well as a brush (128) for assisting with the removal of necrotic tissue.

30 Claims, 16 Drawing Sheets

(52) U.S. Cl.
CPC ............ *A61B 2017/00761* (2013.01); *A61B 2017/320012* (2013.01); *A61B 2217/005* (2013.01); *A61B 2217/007* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,635,035 B1 | 10/2003 | Marasco et al. |
| 6,685,681 B2* | 2/2004 | Lockwood ........ A61F 13/00068 604/305 |
| 6,814,079 B2 | 11/2004 | Heaton et al. |
| 7,070,584 B2* | 7/2006 | Johnson ................ A61M 1/784 602/41 |
| 7,846,141 B2 | 12/2010 | Weston |
| 8,062,273 B2 | 11/2011 | Weston |
| 8,118,815 B2* | 2/2012 | van der Walt ..... A61B 17/1764 606/88 |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 8,998,910 B2* | 4/2015 | Borja ................... A61B 17/155 606/88 |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0122447 A1* | 6/2004 | Harmon ................. A61B 17/54 606/131 |
| 2006/0069343 A1 | 3/2006 | Rontal |
| 2008/0077204 A1 | 3/2008 | Bornstein |
| 2009/0222023 A1 | 9/2009 | Boone, III et al. |
| 2011/0144674 A1 | 6/2011 | Heaton et al. |
| 2014/0163491 A1 | 6/2014 | Schuessler et al. |
| 2015/0080788 A1 | 3/2015 | Blott et al. |
| 2015/0305945 A1* | 10/2015 | Engl ....................... A61F 13/36 112/475.08 |
| 2016/0143660 A1 | 5/2016 | Castro et al. |
| 2017/0007752 A1 | 1/2017 | Freedman et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

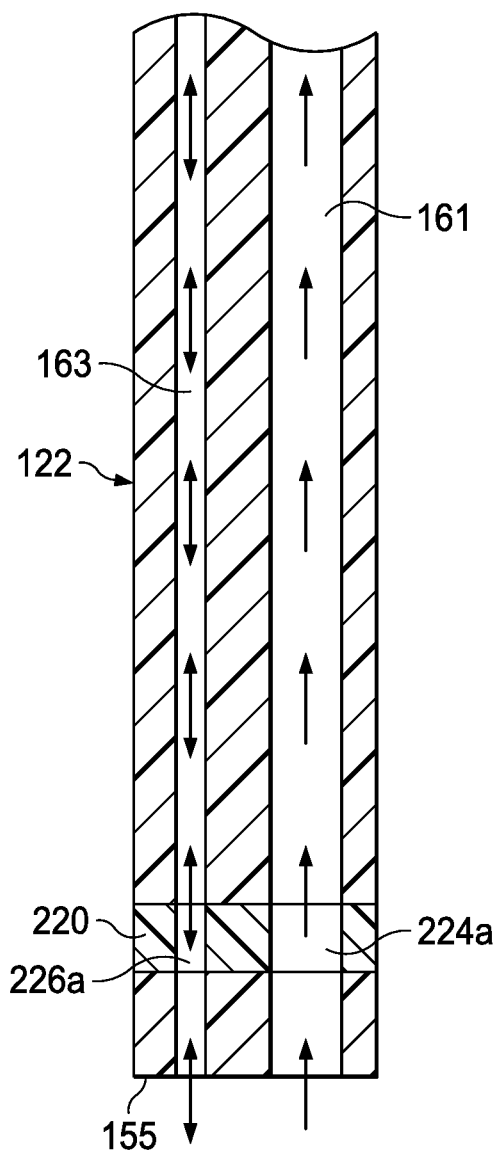 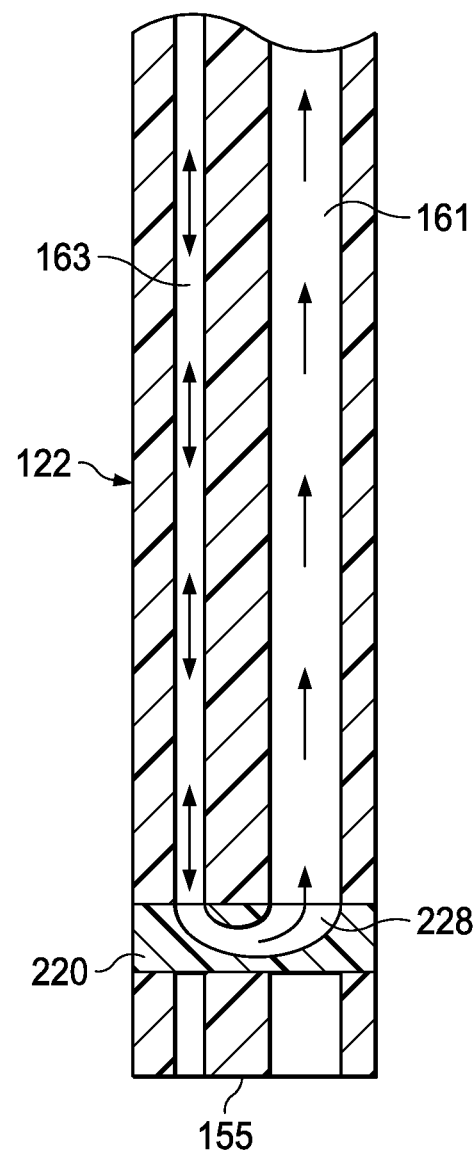
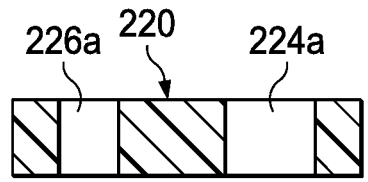 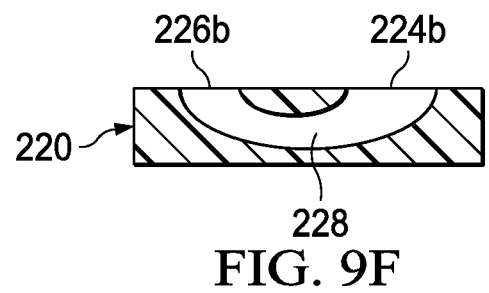
FIG. 9C
FIG. 9E
FIG. 9D
FIG. 9F

WOUND CLEANING TOOL WITH FLUID DELIVERY AND REMOVAL CAPABILITIES

RELATED APPLICATION

This application claims the benefit, under 35 U.S.C. § 119(e), of the filing of U.S. Provisional Patent Application Ser. No. 62/539,366, entitled "WOUND CLEANING TOOL WITH FLUID DELIVERY AND REMOVAL CAPABILITIES," filed Jul. 31, 2017, which is incorporated herein by reference for all purposes.

TECHNICAL FIELD

The invention set forth in the appended claims relates generally to tissue treatment systems and more particularly, but without limitation, to debridement devices, systems, and methods suitable for debriding a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

Similarly, debridement of a tissue site, such as a wound, can be highly beneficial for new tissue growth. Debridement may refer to a process for removing dead, damaged, or infected tissue from a tissue site for improving the healing potential of healthy tissue remaining at the tissue site.

While the clinical benefits of negative-pressure therapy and instillation therapy in conjunction with wound debridement are widely known, improvements to therapy systems, components, and processes may benefit healthcare providers and patients.

BRIEF SUMMARY

New and useful systems, apparatuses, and methods for cleansing and/or debriding a tissue site are set forth in the appended claims. Illustrative embodiments are also provided to enable a person skilled in the art to make and use the claimed subject matter.

In some embodiments, a system for treating a tissue site may include a debridement tool, a negative-pressure source, a fluid source, and a control unit. The debridement tool may have a first end and a second end. The debridement tool may include a first fluid conduit extending from the first end to the second end and a second fluid conduit extending from the first end to the second end. The debridement tool may further include a brush attached to the second end. The negative-pressure source may be fluidly coupled to the first fluid conduit at the first end of the debridement tool. The fluid source may be fluidly coupled to the second fluid conduit at the first end of the debridement tool. The control unit may interface with an operator for receiving and displaying operation parameters of the negative-pressure source and the fluid source.

Other example embodiments may include a method for debriding a tissue site. The method may include positioning a first end of a debridement tool proximate to a portion of necrotic tissue at the tissue site, supplying a treatment fluid through the first end of the debridement tool to the necrotic tissue, and activating a negative-pressure source to deliver negative pressure through the debridement tool to the tissue site.

Other example embodiments may include a system for treating a tissue site having necrotic tissue. The system may include a debridement tool, a negative-pressure source fluidly coupled to the debridement tool, and a fluid source fluidly coupled to the debridement tool.

Additional example embodiments may include a device for debriding a tissue site. The device may include a housing having a first end and a second end. The device may further include a first fluid conduit positioned within the housing and extending from the first end to the second end and adapted to be fluidly coupled to a negative-pressure source. The device may also include a second fluid conduit positioned within the housing and extending from the first end to the second end and adapted to be fluidly coupled to a fluid source. The device may further include a brush attached to the second end.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 9C is a schematic diagram illustrating additional details associated with the rotary valve of FIG. 9A, according to some example embodiments;

FIG. 9D is a cross-section view of a portion of the rotary valve of FIG. 9B;

FIG. 9E is a schematic diagram illustrating additional details associated with the rotary valve of FIG. 9A, according to some example embodiments;

FIG. 9F is a cross-section view of a portion of the rotary valve of FIG. 9B;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
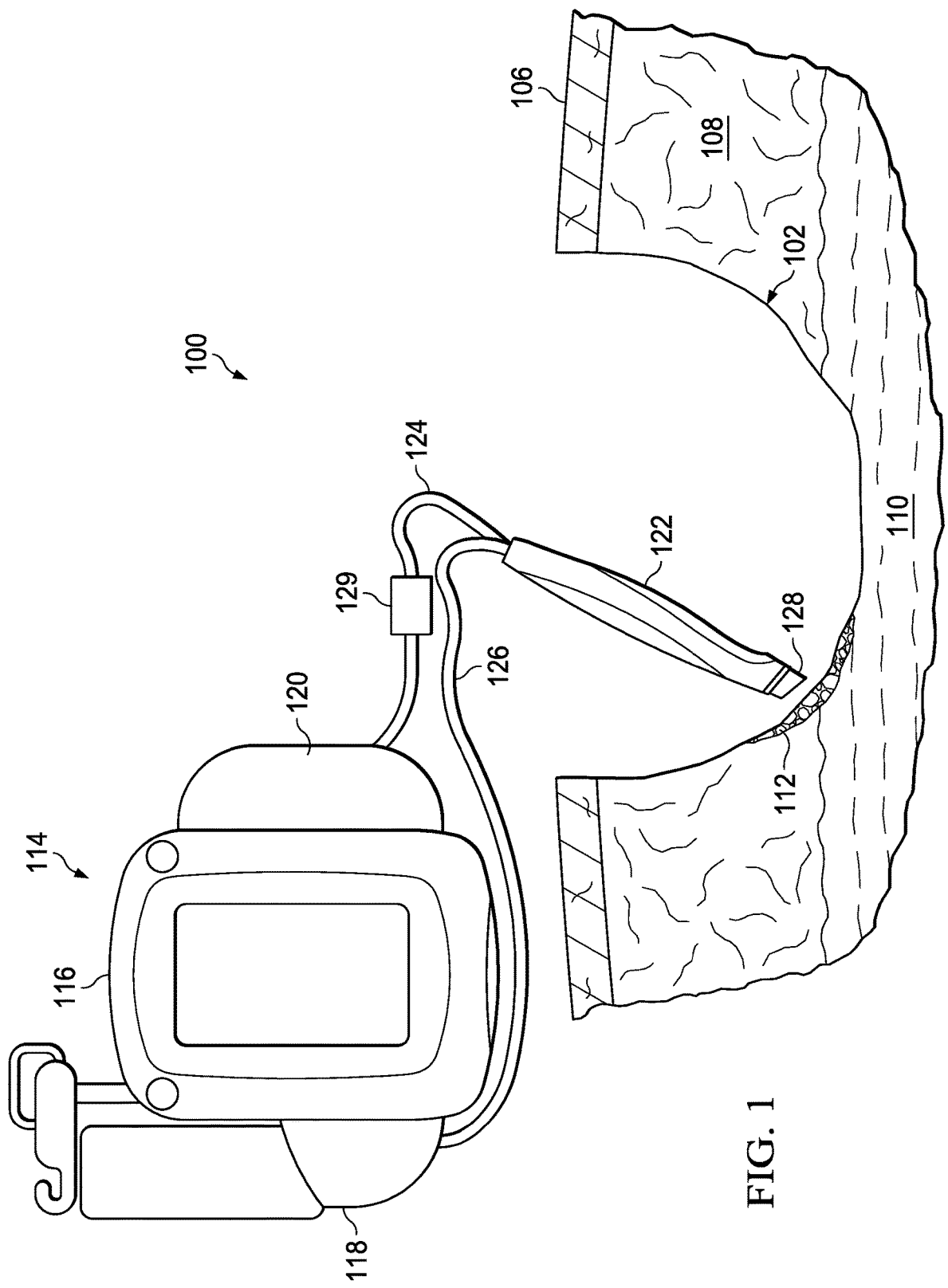
FIG. 1 is a schematic diagram of an example embodiment of a therapy system for treating a tissue site in accordance with this specification.

FIG. 1 illustrates a therapy system 100 that can provide negative-pressure therapy and instillation of topical treatment solutions for treating a tissue site 102. A tissue site in this context may include, without limitation, any irregularity with a tissue, such as an open wound, surgical incision, burn, foreign matter in the tissue, or damaged, necrotic, infected, contaminated, or adherent tissue. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue in which it may be desirable to add or promote the growth of additional tissue. The therapy system 100 is presented in the context of a tissue site 102 which may be through the epidermis 106, or generally skin, and the dermis 108, and reaching into a hypodermis, or subcutaneous tissue 110. The therapy system 100 may be used to treat a tissue site of any depth. Treatment of the tissue site 102 may include removal of fluids, for example, exudate or ascites.

In some embodiments, the tissue site 102 may include necrotic tissue 112, and in many instances, it may be desirable to remove the necrotic tissue 112 in order to promote healing of the tissue site 102. The illustrative, non-limiting embodiment shows the therapy system 100 in the context of the tissue site 102 having a localized, or discrete area, of necrotic tissue 112 within the tissue site 102. The therapy system 100 may also be used in contexts where the tissue site 102 and may include a layer of necrotic tissue 112 that covers the entire surface of a wound.

As used herein, the terms "debride," "debriding," and "debridement," relate to the act of removing or the removal of undesirable tissue, such as, eschar, necrotic, damaged, infected, contaminated, or adherent tissue, or foreign material from a tissue site. Several methods of debridement may be employed to treat a tissue site 102 having necrotic tissue 112, including surgical debridement, mechanical debridement, chemical or enzymatic debridement, and autolytic debridement.

However, each of these methods has both advantages and disadvantages. For example, while mechanical debridement is perhaps the fastest method of debridement, it is almost invariably painful or at least submits the patient to a significant level of discomfort. Additionally, mechanical debridement typically requires a high level of skill from the caregiver.

Chemical, or enzymatic, debridement entails the use of chemical enzymes to convert the necrotic tissue to slough. Chemical debridement may be fast-acting and cause minimal damage to healthy tissue if the chemicals are applied properly. However, chemical debridement has disadvantages as well. The process may be expensive, and traditional chemical debridement methods and systems, such as low pH systems, may be painful to a patient. Other debriding agents, such as papain, may have other health implications and only have limited usage that is restricted by law. Other agents may be used, such as medical grade honey, but can become quickly mobile in the presence of fluid, such as wound exudate, and an applied negative pressure.

Autolytic debridement, or autolysis, entails the use of the body's own enzymes and white blood cells, along with moisture, to hydrate and liquefy the necrotic tissue 112 and slough. Since autolytic debridement is a naturally-occurring process, it is relatively painless and does not risk damage to healthy tissue. Further, autolytic debridement does not require wound fluid to remain in contact with the necrotic tissue 112, and can be facilitated by the use of films, hydrocolloids, and hydrogels. A disadvantage of autolytic debridement is that autolytic debridement is slower than other types of debridement, rendering the wound susceptible to infection.

Currently, mechanical debridement, such as with sharp instruments, is the standard of care for wound debridement, which involves cleaning the wound and removing dead or infectious tissue using a blade. However, because not all caregivers are qualified or authorized to perform sharp debridement, patients may often be required to wait for a scheduled time with a surgeon clinician for the wound to be debrided in a surgical environment. In many situations, it would be advantageous to have the wound cleaned and debrided with a simple hand tool, such as a curette. However, such an option can be messy and, in particular, it is often difficult to ensure that all of the detritus has been removed from the wound before it is dressed.

Thus, a simple and effective way for cleaning and debriding a wound that may be performed away from a surgical environment may be beneficial. Ideally, the cleansing and debridement process may be performed by a skilled nurse or caregiver, without having to wait for a sharp, mechanical debridement process. A solution that allows for reaching challenging tissue site locations or immobile patients may also be beneficial. Moreover, it may be desirable to have a system and method that can be combined with negative-pressure applications. The therapy system 100 may address these outstanding needs and others. For example, the therapy system 100 may provide a low-pain alternative for enhanced debridement and healing of tissue sites that can be used in conjunction with negative-pressure treatment.

The therapy system 100 may include a therapy unit, a negative-pressure source, a fluid source, and a debridement tool. For example, as illustrated in FIG. 1, in some embodiments, a therapy unit 114 may include a negative-pressure source 116 and a fluid source 118, as well as a container 120, any or all of which may be fluidly coupled to a debridement tool 122. In some embodiments, the therapy unit 114 may be a V.A.C.ULTA™ Therapy Unit, available from Kinetic Concepts Inc., of San Antonio, Tex., USA.

In general, components of the therapy system 100 may be coupled directly or indirectly. For example, the negative-pressure source 116 may be directly coupled to the container 120, and indirectly coupled to the debridement tool 122 through the container 120. In some embodiments, components may be coupled by virtue of physical proximity, being integral to a single structure, or being formed from the same piece of material. Coupling may also include mechanical, thermal, electrical, or chemical coupling (such as a chemical bond) in some contexts.

Components may also be fluidly coupled to each other to provide a path for transferring fluids (i.e., liquid and/or gas) between the components. In some embodiments, for example, components may be fluidly coupled through a tube. A "tube" as used herein, broadly refers to a tube, pipe, hose, conduit, or other fluid conductor with one or more lumina or open passages adapted to convey fluid between two ends. Typically, a tube is an elongated, cylindrical structure with some flexibility, but the geometry and rigidity may vary. Moreover, some fluid conductors may be molded into or otherwise integrally combined with other components.

The fluid mechanics of using a negative-pressure source to reduce pressure in another component or location can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

A negative-pressure supply, such as the negative-pressure source 116, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 116 may be combined with a controller and other components into a therapy unit, such as therapy unit 114. A negative-pressure supply may also have one or more supply ports configured to facilitate coupling and de-coupling the negative-pressure supply to one or more distribution components. For example, the negative-pressure source 116 may be fluidly coupled to the debridement tool 122 by a negative-pressure conduit 124.

The therapy system 100 may also include a source of instillation solution, such as a therapeutic solution useful for debridement. For example, the fluid source 118 may be fluidly coupled to the debridement tool 122 by a supply conduit 126, as illustrated in the example embodiment of FIG. 1. The fluid source 118 may also be representative of a container, canister, pouch, bag, or other storage component, which can provide a solution for instillation therapy. Compositions of solutions may vary according to a prescribed therapy, but examples of solutions that may be suitable for some prescriptions may include a saline solution. Other solutions may include sterile water, lactated ringers solution, and/or commercial wound cleansers.

The fluid source 118 may be housed within or used in conjunction with other components to facilitate movement of a fluid. The fluid source 118 may be, or include, a fluid pump, such as a peristaltic pump. Additionally or alternatively, in some embodiments, the fluid source 118 may be a fluid reservoir, which may store and deliver fluid. In any embodiment, the fluid source 118, such as a fluid pump or a fluid reservoir, may include a container, such as a canister, pouch, or other storage component.

The container 120 is representative of a container, canister, pouch, or other storage component, which can be used to manage exudate and other fluid withdrawn from a tissue site. In many environments, a rigid container may be preferred or required for collecting, storing, and disposing of fluid. In other environments, fluids may be properly disposed of without rigid container storage, and a re-usable container could reduce waste and costs associated with negative-pressure therapy. In some preferred embodiments, the container 120 may be positioned in fluid communication between the negative-pressure source 116 and the debridement tool 122 to collect fluid drawn from the tissue site 102 by the debridement tool 122 and through the negative-pressure conduit 124. The container 120 may also include features that enable filtering of the effluent that is withdrawn from the tissue site 102. In some embodiments, the container 120 may attach to the therapy unit 114, as illustrated in FIG. 1. The container 120 may include multiple ports and connection interfaces for integration with the therapy unit 114, the negative-pressure source 116, the fluid source 118, the debridement tool 122, and/or the other components of the therapy system 100.

The debridement tool 122 may include a collection of fluid conduits for the application of negative pressure and the delivery of fluid to the tissue site 102. In some embodiments, the debridement tool 122 may be fluidly connected to the negative-pressure source 116 by the negative-pressure conduit 124. Additionally, the debridement tool 122 may be fluidly connected to the fluid source 118 by the supply conduit 126. In some embodiments, the debridement tool 122 may include a brush 128.

The therapy system 100 may also include a particulate filter 129, which may be positioned in fluid communication between the negative-pressure source 116 and the debridement tool 122, and in some embodiments between the container 120 and the debridement tool 122. The particulate filter 129 may function to remove particulate matter from the effluent that has circulated through the tissue site 102. For example, in the embodiment pictured in FIG. 1, fluid delivered to the tissue site 102 by the fluid source 118 through the supply conduit 126 and the debridement tool 122 may be drawn back out of the tissue site 102 by the debridement tool 122 and transported through the negative-pressure conduit 124 to the particulate filter 129. The fluid may be filtered to remove particulate matter in the particulate filter 129, before being recollected in the container 120.

Figure 2:
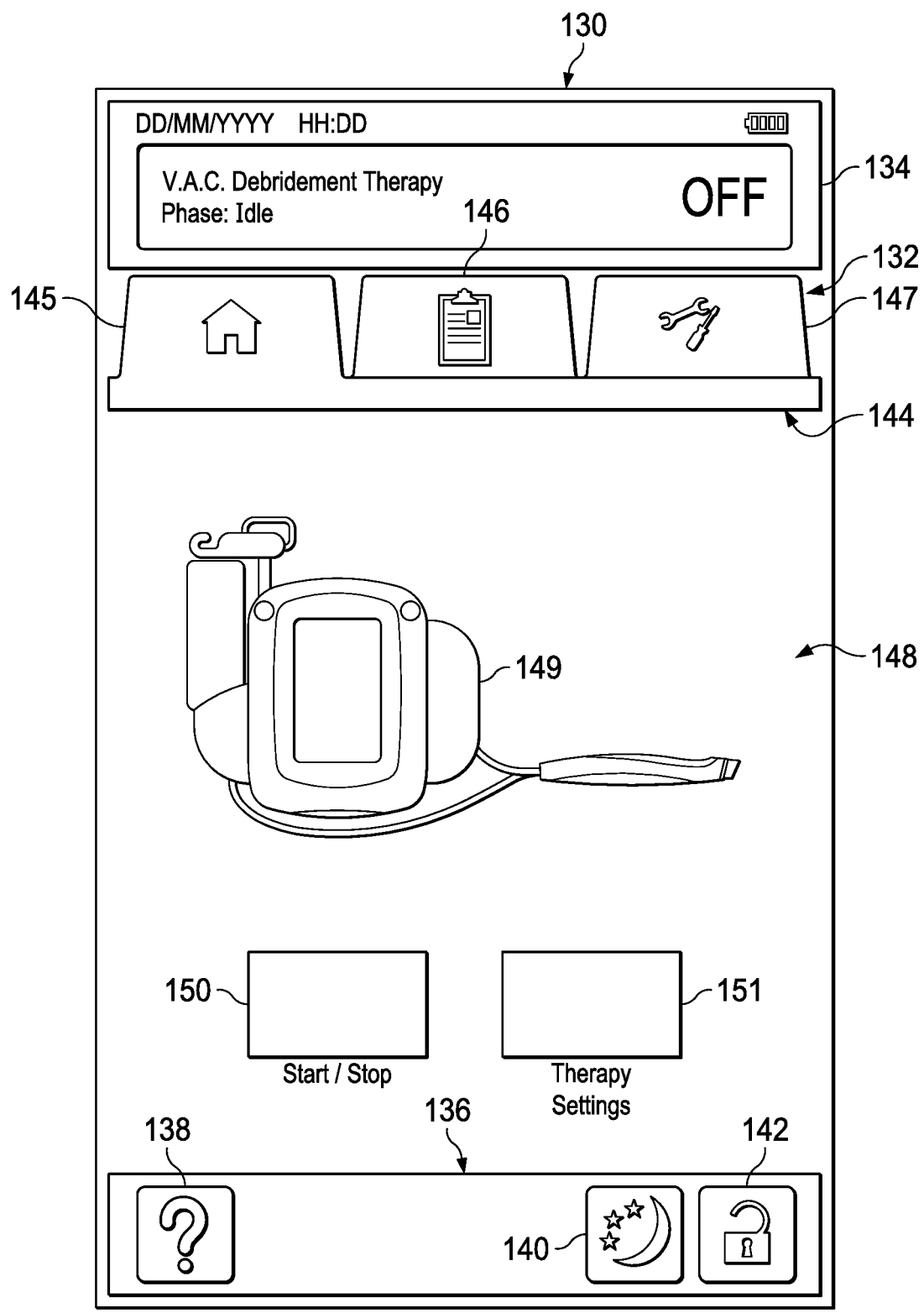
FIG. 2 is a diagram of a graphical user interface (GUI) that may be associated with an example embodiment of the therapy system of FIG. 1.

FIG. 2 is a diagram of an example of a graphical user interface (GUI) 130, illustrating additional details that may be associated with some embodiments of the therapy unit 114. In some embodiments, the GUI 130 may display an example embodiment of a debridement application, which may allow an operator to receive information from and control the therapy unit 114 as well as other components of the therapy system 100. In some embodiments, the GUI 130 may be configured to display features of a debridement application as part of a debridement view 132. For example, the debridement view 132 of the debridement application may include a variety of display and information fields as well as soft-buttons for controlling the debridement and negative-pressure functionalities of the therapy unit 114, as part of the therapy system 100. For example, the debridement view 132 may include a header bar 134, which may provide the operator, such as a clinician, with general operating status information of the therapy unit 114 as well as the overall therapy system 100. The header bar 134 may include information fields which relate to the operation mode of the therapy unit 114, the phase of the specific operation mode, as well as whether one or more pump devices, such as the negative-pressure source 116, are currently operating. Additionally, the header bar may also display the general date and time information of the therapy unit 114, and where applicable, a battery status indicator for the therapy unit 114.

The operator may also be presented with a toolbar 136, which may be located across the bottom of the debridement view 132, in some illustrative embodiments. The toolbar 136 of the debridement view 132 may include a number of selectable graphical elements, including a "Help" soft-button 138, a "Night-Mode" soft-button 140, and a "Lock" soft-button 142, along with soft-buttons assigned to any other features related to debridement therapy. The operator may select any of these functions (i.e., help, night-mode, lock) to cause another graphical user interface for performing the selected function to be presented to the operator. For example, the "Help" soft-button 138 may allow an operator to access a user guide as well as allow the operator to send questions or comments to a clinical or technical support team member at a remote support center. The "Night-Mode" soft-button 140 may allow the operator to dim or turn-off the backlight for the screen or monitor displaying the GUI 130. The "Lock" soft-button 142 may allow an operator to securely log out of the debridement therapy application, as well as lock access to interfacing with the GUI 130 of the therapy unit 114.

In the main portion of the GUI 130, the operator may be presented with a menu bar 144, which may display one or more "tabs" soft-buttons, for accessing various features and functionalities of the selected therapy mode, such as the debridement mode shown in the example illustrative embodiment of FIG. 2. For example, the menu bar 144 may include a "Home" tab soft-button 145, a "Treatment Protocol" tab soft-button 146, and a "Tools" tab soft-button 147. As shown in the illustrative embodiment of FIG. 2, the "Home" tab soft-button 145 may display a home view 148 showing high-level summary information for the current operational mode of the therapy unit 114. For example, therapy icon 149 may display a graphic of the therapy mode, which in the case of FIG. 2 is debridement tool therapy. Additionally, the home view 148 associated with the "Home" tab soft-button 145 may also display a start/stop soft-button 150, which may be used to activate and deactivate the functions of the therapy system 100 related to the selected therapy mode, and a therapy settings soft-button 151. The therapy settings soft-button 151 may allow an operator to view and modify a variety of different parameters, such as negative-pressure application, fluid delivery, or debridement operation, which may relate to many of the individual components of the therapy system 100.

The "Treatment Protocol" tab soft-button 146 may allow an operator to access a variety of different views related to the prescribed and/or selected treatment regimen(s) for one or more tissue site(s). Through this tab, the operator may also be able to view instructions provided by treating physicians or other clinicians, as well as notes entered by previously-treating caretakers. Additionally, the operator may be able to enter date- and time-stamped notes, instructions, or reminders for future caretakers, such as clinicians. The "Tools" tab soft-button 147 may allow the operator to select from a variety of different options related to display settings, power-management settings, and troubleshooting options. It should be understood that the GUI 130 is exemplary and that additional and/or alternative functions and selection elements may be provided to the operator.

Figure 3:
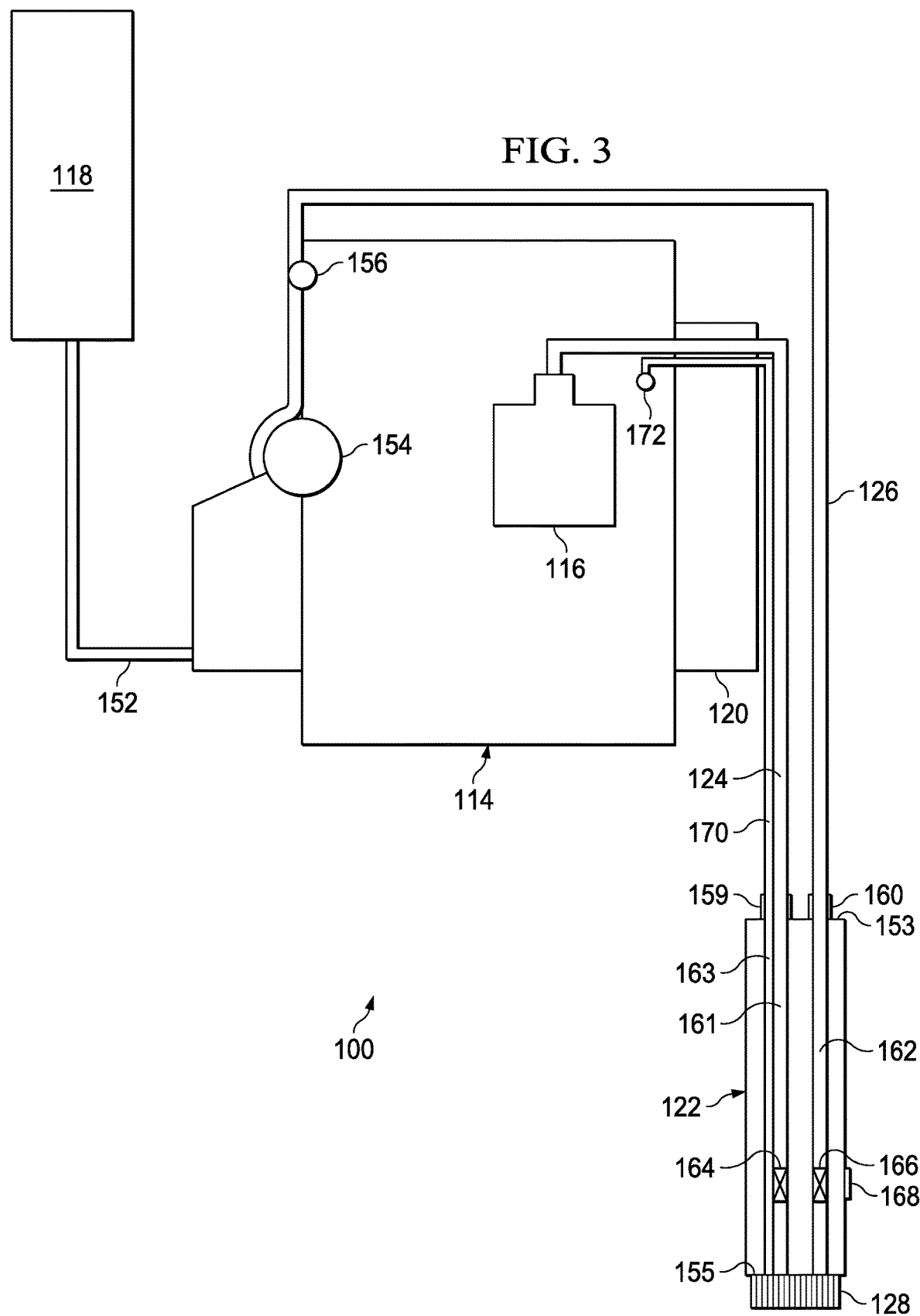
FIG. 3 is a schematic diagram illustrating additional details that may be associated with some example embodiments of the therapy system of FIG. 1.

FIG. 3 is a schematic diagram of another example of the therapy system 100, illustrating additional details that may be associated with some embodiments. In the illustrative example of FIG. 3, the negative-pressure source 116 is depicted as being housed inside of the therapy unit 114. Further, in the example embodiment of FIG. 3, the fluid source 118 is depicted as a freestanding unit that is fluidly connected to the therapy unit 114 by feeder conduit 152. However, in other embodiments, the fluid source 118 may be physically attached to the therapy unit 114 via brackets, a holster, or other mechanical means, and may include an interface for fluidly coupling to the therapy unit 114.

The debridement tool 122 may be in the form of a handheld tool, such as a wand, for providing both negative pressure as well as a treatment fluid to a tissue site or wound, such as the necrotic tissue 112 of tissue site 102 of FIG. 1. As depicted in FIG. 3, the debridement tool 122 may be in fluid communication with the negative-pressure source 116 by negative-pressure conduit 124 and may be in fluid communication with the fluid source 118 via supply conduit 126. In some embodiments, such as the illustrative embodiment of FIG. 3, the debridement tool 122 may be fluidly connected to the negative-pressure source 116 by means of container 120, in which case the path of the negative-pressure conduit 124 may be from the debridement tool 122 to the container 120, with the container 120 also fluidly connected to the negative-pressure source 116. Similarly, in some embodiments, the debridement tool 122 may be fluidly connected to the fluid source 118 by means of components of the therapy unit 114, such as a fluid pump 154.

In some embodiments, the debridement tool 122 may be constructed from an injection-molded casing that may be fitted with a rubber grip. The debridement tool 122 may be formed in two halves, which may be snap-fitted together. Internally, the debridement tool 122 may include conduits, such as tubes, for conducting negative-pressure and treatment fluid through the body of the debridement tool 122. For example, the debridement tool 122 may include a negative-pressure tube 161, a treatment fluid tube 162, and in applicable embodiments, a pressure-sensing tube 163. Internally, these tubes may be securely housed within ribbing of the casing material of the debridement tool 122.

In some embodiments, the debridement tool 122 may have a connector end 153 and an applicator end 155. The debridement tool 122 may be directly fitted with tubing connectors at the connector end 153 for attaching the negative-pressure conduit 124 and supply conduit 126 to the body of the debridement tool 122. For example, the debridement tool 122 may include a first connector 159 for fluidly connecting the negative-pressure conduit 124 and may include a second connector 160 for fluidly connecting the supply conduit 126 to the debridement tool 122. In some embodiments, where applicable, the first connector 159 may also be sized and configured to additionally attach a pressure-sensing conduit 170.

The debridement tool 122 may include multiple valves for controlling the delivery of either or both of negative-pressure and a treatment fluid to the applicator end 155 of the debridement tool 122. For example, the debridement tool 122 may include a fluid removal valve 164, which may act on the negative-pressure tube 161 for regulating the application of negative-pressure to the applicator end 155 of the debridement tool 122, and ultimately to the tissue site 102. The debridement tool 122 may also include a fluid delivery valve 166, which may control the flow of treatment fluid through the treatment fluid tube 162 to the applicator end 155 of the debridement tool 122.

Additionally, the debridement tool 122 may include a brush 128 at the applicator end 155, for allowing a user to apply a scrubbing or abrasive force to a portion of a wound, such as necrotic tissue 112 of tissue site 102. In some embodiments, the brush 128 may be made from a medical-grade nylon material. The brush 128 may be fitted with a snap fitting, which may allow for brush heads to be interchanged for replacement heads of different grades, with the grades being determined by different material lengths, diameters, and hardness of the heads. The interchangeability of the brush heads may allow for use of the debridement tool 122 on a wider range of tissue sites, including wounds. Different grades of brush heads may also be effective for different purposes when cleaning and/or debriding a particular wound. For example, brush heads in some embodiments may have bristles that may range from 4 mm to 20 mm in length and from 0.10 mm to 0.50 mm in diameter. Testing of different grades of nylon brush heads has shown that soft brushes (~0.17 mm×9 mm bristles) clean the wound by providing a softer debridement tool for wounds with more exudate and slough as opposed to hard eschar. Additionally, testing has shown that firm brushes (~0.25 mm×9 mm bristles) clean wounds with more exudate and slough as well as can provide some cleaning and debridement to wounds with some amount of hard eschar present. Meanwhile, hard brushes (~0.17 mm×6 mm bristles) have been shown to clean and debride wounds with hard eschar. The hardness or firmness of the bristles on the brush head may be selected depending on the particular tissue site in need of debridement.

The debridement tool 122 may further include at least one control button, such as first control button 168, for allowing an operator to control the delivery of treatment fluid, and/or the supply of negative pressure, when applicable. Depending on the configuration, the first control button 168 may function to open/close the fluid delivery valve 166, the fluid removal valve 164, or both. In some embodiments, the first control button 168 may also be configured to activate/deactivate the fluid pump 154 and/or the negative-pressure source 116.

As shown in this embodiment of FIG. 3, the therapy system 100 may also include a pressure-sensing functionality, for providing feedback to the therapy unit 114 and the operator as to when certain target or threshold pressure levels have been reached. For example, the therapy system 100 may include a pressure-sensing conduit 170, which may provide fluid communication between the debridement tool 122 and a pressure sensor 172.

The therapy system 100 may be further equipped with a flow sensor 156 for monitoring the flow rate of the treatment fluid originating from the fluid source 118. In embodiments which include a fluid pump, such as the fluid pump 154 shown in FIGS. 3 and 4, the flow sensor 156 may monitor the flow rate of the treatment fluid pumped by the fluid pump 154 through the supply conduit 126 to the debridement tool 122. The flow sensor 156 may thus be configured to detect a fluid blockage along the flow path of the fluid, as well as communicate to a control logic of the therapy unit 114 to temporarily halt the operation of the fluid pump 154 to stop the fluid flow.

The functionality of the flow sensor 156 may also be indirectly linked to the one or more control buttons of the debridement tool 122. For example, when the first control button 168 is set to the "off" position, thus closing the fluid delivery valve 166 and disrupting the flow of fluid through the treatment fluid tube 162 and supply conduit 126, the flow sensor 156 may detect this change in fluid flow and send a signal to stop the fluid pump 154 from pumping. In some embodiments, the therapy system 100 may be configured to differentiate between unintentional fluid blockages and blockages due to the closure of the fluid delivery valve 166 directed by an operator. While in cases of unintentional blockages, the fluid pump 154 may have to be powered-off and manually reset. In the situation where the blockage is due to the closure of the fluid delivery valve 166, the control logic of the fluid pump 154 may be programmed so that the fluid pump 154 may automatically attempt to resume pumping fluid through the system at regular intervals, for example in intervals of about 1-2 seconds. The fluid pump 154 may thus recommence delivery of treatment fluid once the fluid delivery valve 166 has been returned to the open position.

Figure 4:
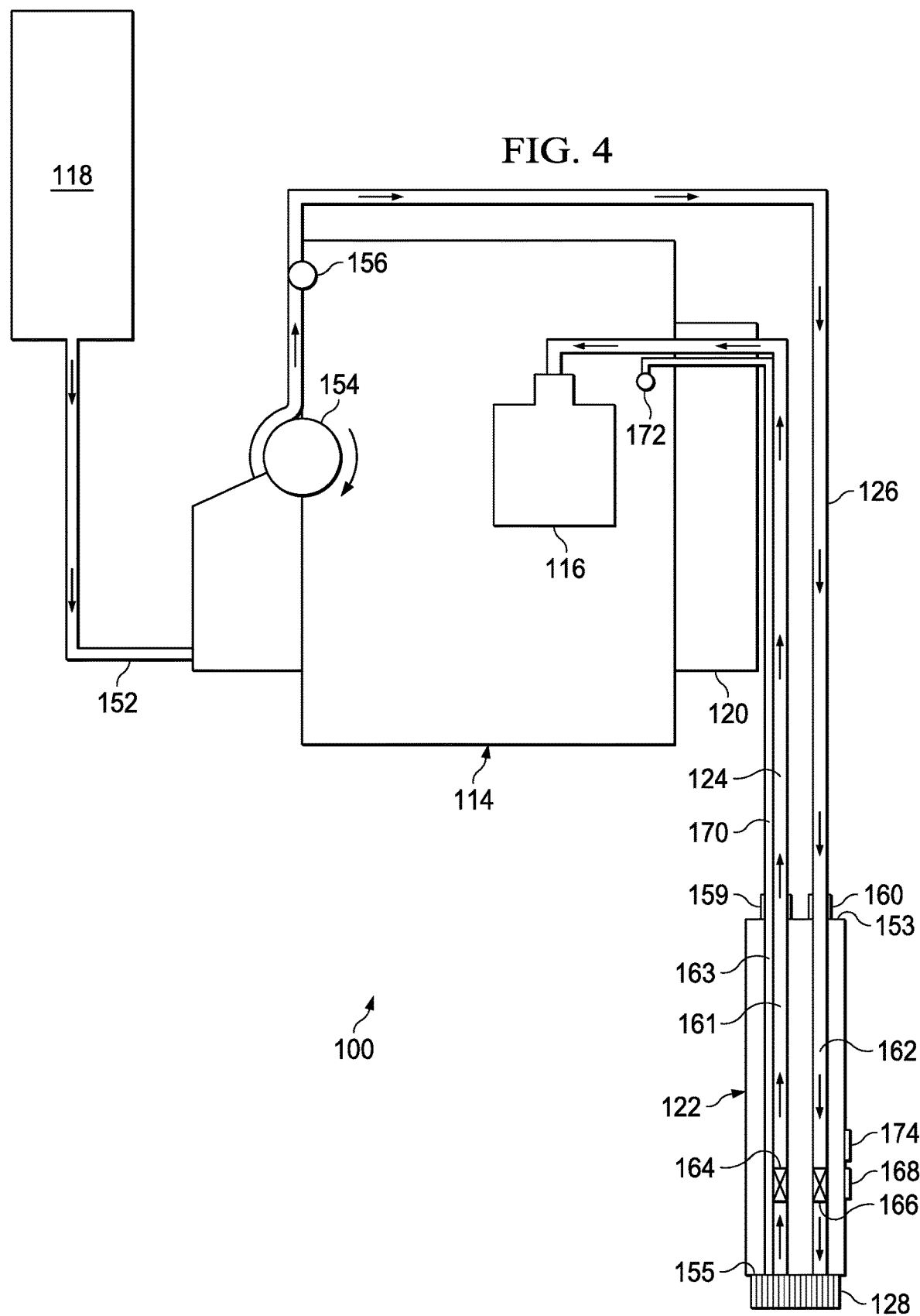
FIG. 4 is a schematic diagram illustrating additional details that may be associated with some example embodiments of the therapy system of FIG. 1.

Referring now also to FIG. 4, some embodiments of the debridement tool 122 may include a second control button 174. In embodiments including two control buttons, both the first control button 168 and the second control button 174 may be operable to control the valves within the debridement tool 122. For example, the first control button 168 may be operable to activate the fluid delivery valve 166 to open a fluid pathway through the debridement tool 122 to allow fluid to flow through the treatment fluid tube 162 to the applicator end 155 of the debridement tool 122 and out to the tissue site 102. The second control button 174 may operate to activate the fluid removal valve 164 to provide an open passageway for negative-pressure to be delivered through the negative-pressure tube 161 and to the applicator end 155 of the debridement tool 122. In some applicable embodiments, the second control button 174 may also activate the fluid removal valve 164 to open the passageway through the pressure-sensing tube 163. The inclusion of two control buttons may allow an operator to conveniently choose to independently deliver fluid and apply negative pressure, or administer both simultaneously.

While the normal, resting position of the control buttons may be in an "off" position, the buttons may be turned to an "on" position either momentarily or for a continuous period of time. For example, some embodiments of the debridement tool 122 may include control buttons that have a "depress-and-lock" feature, so that the control buttons may be depressed for intermittent activation of the "on" position, or depressed and locked into a continuous "on" position. In some preferred embodiments, the control buttons may be fitted on a top side of the debridement tool 122 to allow for thumb control by an operator during operation of the tool.

In operation, an operator may connect the therapy unit 114, including the negative-pressure source 116 and the fluid source 118, to the debridement tool 122 using conduits, such as the negative-pressure conduit 124 and supply conduit 126, as well as connectors on the debridement tool 122, such as the first connector 159 and the second connector 160. Once the various components of the therapy system 100 are connected, the operator may select and activate a debridement mode using on-screen soft-buttons from the GUI 130 of the therapy unit 114. Once the debridement mode has been selected by the operator and activated, a debridement view 132 may be displayed on the GUI 130 to the operator. The on-screen buttons, as described above, may be used to start and stop debridement therapy as appropriate.

Once debridement therapy has been initiated, the fluid pump 154 may initiate at a slow rate, which, for example, may be at a delivery rate of approximately 35% duty of 1.6 ml/sec flow rate. The user may then control the delivery of fluid from the debridement tool 122, using a control button positioned on the debridement tool 122, such as the first control button 168, to open the fluid delivery valve 166. The fluid pump 154 may then pump fluid from the fluid source 118, which may be a fluid supply bag, until the fluid source 118 has been emptied, or until the operator closes the fluid delivery valve 166 by setting the first control button 168 to an "off" position. The fluid, which may be a saline-based solution, may exit the applicator end 155 of the debridement tool 122 into the tissue site 102, where the fluid may cleanse and/or debride the necrotic tissue 112. The fluid may assist with washing away the necrotic tissue 112 as the brush 128 is used to dislodge and remove portions of the necrotic tissue 112. Additionally, the instilled fluid may serve to moisten and loosen the necrotic tissue 112 so as to reduce discomfort during removal by the brush 128. The fluid also may provide a mechanism for dry particulates removed from the necrotic tissue 112 or other portions of the tissue site 102 to exit the tissue site 102. As mentioned, the fluid may be a saline-based solution, however the fluid may also include additional solutions such as PRONTOSAN solution or NEUTROPHASE cleanser, available from NovaBay Pharmaceuticals. Following debridement of the necrotic tissue 112 by the fluid, the remaining effluent may be drawn out of the tissue site 102 by negative pressure applied by the negative-pressure source 116 through the negative-pressure conduit 124 and the negative-pressure tube 161 of the debridement tool 122. For example, the operator may control the removal of fluid through the debridement tool 122 using the second control button 174 to open the fluid removal valve 164 to provide an open passageway for negative pressure to be delivered through the negative-pressure tube 161 and to the applicator end 155 of the debridement tool 122. The effluent may enter and pass through the negative-pressure tube 161 of the debridement tool 122, and then pass through the negative-pressure conduit 124 to the particulate filter 129, if applicable, where particulate matter may be filtered out of the effluent. The filtered fluid may then be collected by the container 120.

Thus, the therapy system 100 may store any particulate matter in a convenient location for disposal.

Figure 5:
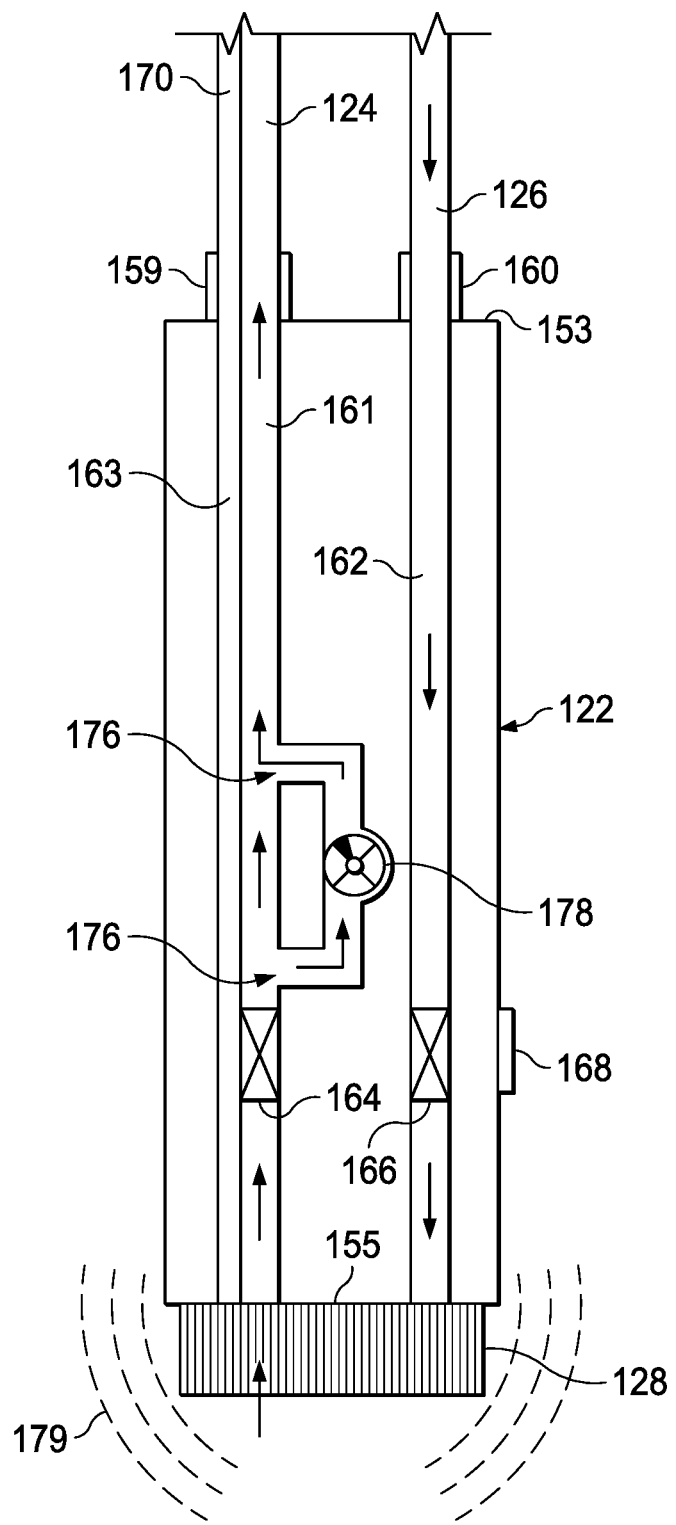
FIG. 5 is a schematic diagram illustrating additional details that may be associated with features of some example embodiments of the therapy system of FIG. 1.

FIG. 5 illustrates an example embodiment of the debridement tool 122, which includes a built-in oscillation feature. In this illustrative embodiment, the internal negative-pressure tube 161 of the debridement tool 122 may be modified to include an oscillation pathway 176, to detour a portion of the flow that would ordinarily pass solely through the negative-pressure tube 161. The oscillation pathway 176 may run in parallel to a portion of the negative-pressure tube 161. Incorporated in the oscillation pathway 176 may be a rotating weight 178. The rotating weight 178 may be an offset weight that rotates under the forces generated by fluid flow through the oscillation pathway 176, in order to cause axial oscillation, depicted by oscillation waves 179 in FIG. 5. In some embodiments, the rotating weight 178 may be protected from potential damage resulting from contact with fluid and exudate materials passing through the negative-pressure tube 161 of the debridement tool 122 by the inclusion of filters as part of the negative-pressure tube 161, or more specifically, included in the oscillation pathway 176. The debridement process may be benefitted by the inclusion of the oscillation feature, as the time required to clean and debride a wound site may be decreased due to increased device efficiency, and therefore, user effort may be reduced by decreasing the amount of manual force required to be applied to the wound site by the operator. Alternatively or additionally, the built-in oscillation feature may include oscillation provided by a powered mechanical or electrical means, such as a powered off-centered weight or powered motor driving a cam and gear assembly to provide a back-and-forth motion.

Figure 6:
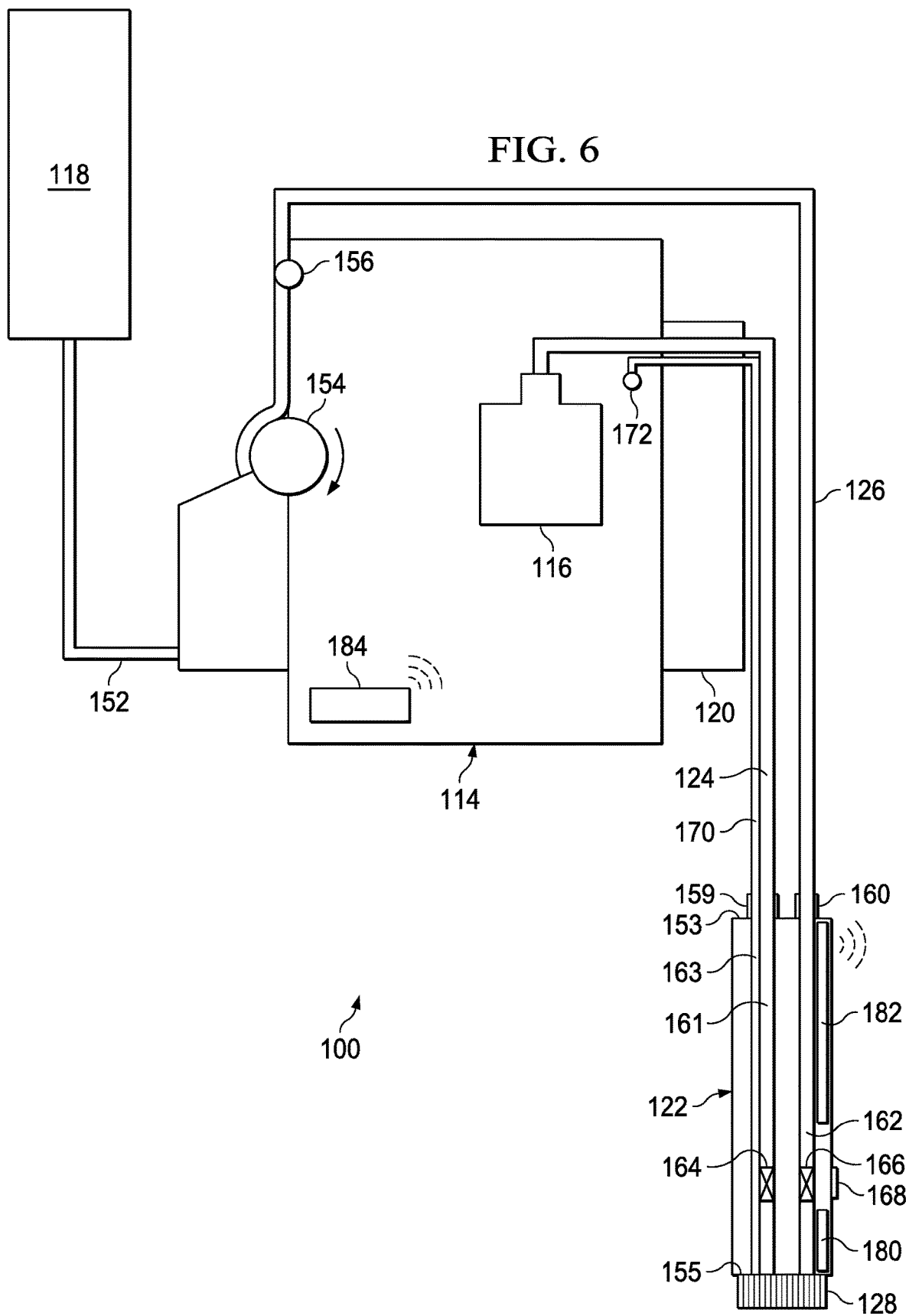
FIG. 6 is a schematic diagram illustrating additional details that may be associated with features of some example embodiments of the therapy system of FIG. 1.

FIG. 6 illustrates an example embodiment of the therapy system 100 configured with wireless communication capabilities for exchanging data between the debridement tool 122 and the therapy unit 114. The wireless communication may allow for control of the various fluid-delivery and negative-pressure application components of the therapy system 100. As part of the wireless communication functionality, some embodiments of the debridement tool 122 may include a power source 180 and a communications transceiver 182. The communications transceiver 182 may be configured to communicate via a wireless communications protocol, such as Bluetooth® or ZigBee®, with a communications device 184 which may be incorporated into the therapy unit 114. For example, as previously discussed with respect to FIGS. 3-5, the delivery of fluid from the debridement tool 122 may be controlled using the first control button 168 to open the fluid delivery valve 166. When the fluid delivery is turned "on," the communications transceiver 182 may send a wireless signal to the communications device 184 of the therapy unit 114 in order to start the fluid pump 154. Once the fluid pump 154 has begun, fluid may be instilled through the supply conduit 126 to the debridement tool 122 and then out the applicator end 155 of the debridement tool 122 at a fixed delivery rate (~35% duty of 1.6 mL/sec flow rate). When the operator wants to deactivate the fluid pump 154, once again, a wireless signal may be sent from the communications transceiver 182 to the communications device 184 of the therapy unit 114 to turn "off" the fluid pump 154. In some embodiments, the "on" and "off" control may also be controlled through the GUI 130 of the therapy unit 114. In such embodiments, upon input from the operator, the communications device 184 may send a wireless signal to the communications transceiver 182 in the debridement tool 122 to control the positioning of the fluid delivery valve 166.

Similar to the control of the fluid delivery using wireless signals from the debridement tool 122, the supply of negative pressure from the negative-pressure source 116 may also be controlled using wireless protocols. For example, an operator may depress the second control button 174 in order to open the fluid removal valve 164. When the second control button 174 is turned to the "on" position, the communications transceiver 182 may send a wireless signal to the communications device 184 of the therapy unit 114, in order to start the negative-pressure source 116. The negative-pressure source 116 may provide negative pressure through the negative-pressure conduit 124 and to the debridement tool 122, until the time at which the operator may return the second control button 174 to an "off" position to close the fluid removal valve 164 and to send a wireless signal from the communications transceiver 182 to the communications device 184 to deactivate the negative-pressure source 116. Further, in some embodiments, the wireless control functionality of the debridement tool 122 may also be used to indirectly control the oscillation feature through the control of the negative-pressure source 116 and fluid removal valve 164.

Figure 7A:
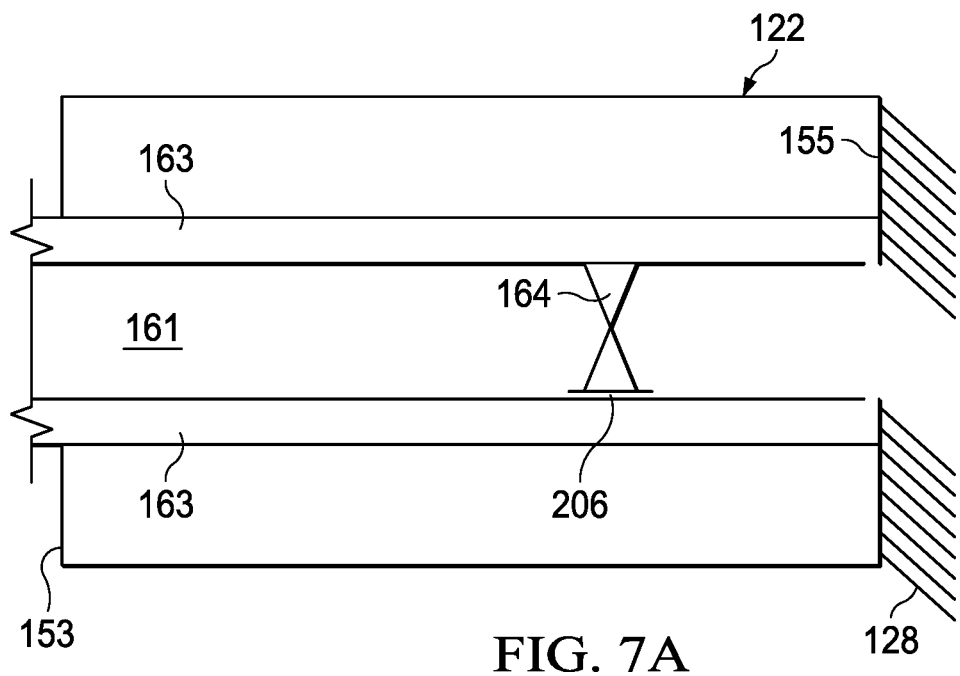
FIG. 7A is a schematic diagram illustrating additional details that may be associated with some example embodiments of the therapy system of FIG. 1.
Figure 7B:
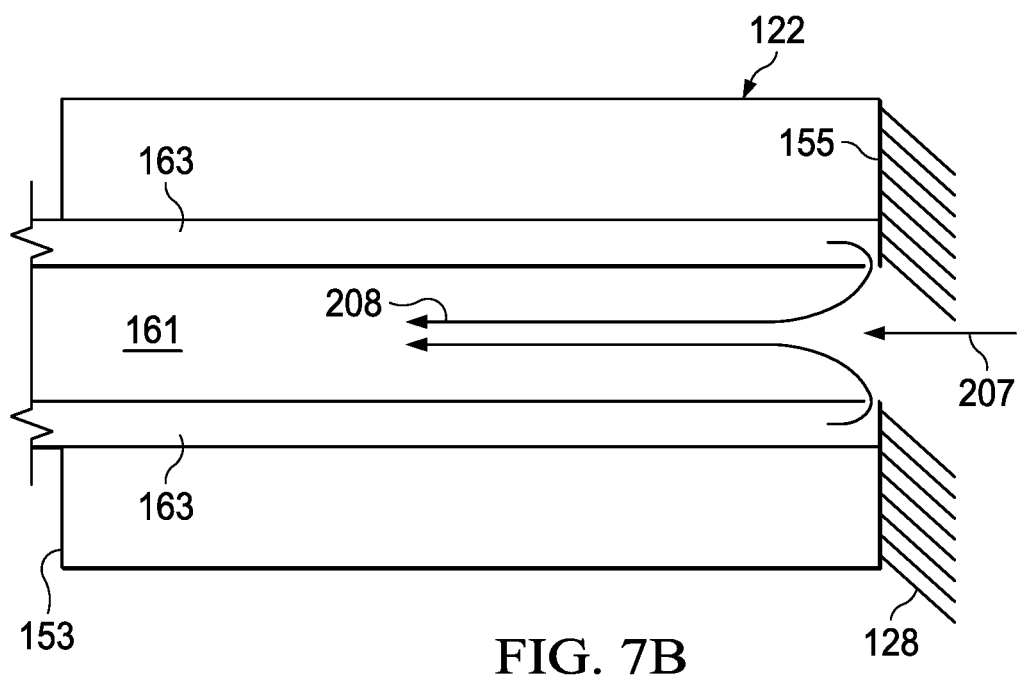
FIG. 7B is a schematic diagram illustrating additional details that may be associated with some example embodiments of the therapy system of FIG. 1.

Referring now to FIGS. 7A-7B, portions of an example embodiment of the debridement tool 122 and therapy system 100 are shown, illustrating certain pressure-sensing features and functionality. More specifically, FIGS. 7A-7B illustrate the effects on pressure experienced at different locations of the passageways of the debridement tool 122, such as the negative-pressure tube 161 and one or more pressure-sensing tube(s) 163, in response to a fluid valve, such as fluid removal valve 164, being open or closed. Referring now primarily to FIG. 7A, it can be seen that fluid removal valve 164 positioned within the negative-pressure tube 161 is positioned in a closed configuration. In such a closed position, fluid removal valve 164 may substantially obstruct the fluid communication between a downstream side, or space between the fluid removal valve 164 and the negative-pressure source 116, of the negative-pressure tube 161 and an environment exterior to the debridement tool 122, or upstream side of the fluid removal valve 164. In the example embodiment of FIG. 7A, pressure measurements may be taken at two different portions of the debridement tool 122. A first pressure may refer to a pressure within at least one pressure-sensing tube 163. For example, the first pressure may be determined by a pressure sensor that is connected to at least one pressure-sensing tube 163. While in some embodiments there may be one pressure-sensing tube 163, additional embodiments may include two or more pressure-sensing tubes 163. For example, in one example embodiment, the debridement tool 122 may include four pressure-sensing tubes 163. In embodiments having more than one pressure-sensing tube 163, a single pressure sensor may be in fluid communication with the multiple pressure-sensing tubes 163. For example, in some embodiments, the debridement tool 122 may include four pressure-sensing tubes 163, which may be fluidly connected to a pressure sensor, such as pressure sensor 172 of FIG. 3, via a conduit, such as pressure-sensing conduit 170. While each of the pressure-sensing tubes 163 may be sized in a way that should minimize the chance of blockage, including multiple tubes may allow for continued pressure sensing despite one or more becoming blocked or occluded.

A second pressure may refer to a pressure within the negative-pressure tube 161, and more specifically the pressure downstream from the fluid removal valve 164. Thus, the second pressure may correspond to a pressure within a container or canister for collecting exudates from a tissue site, such as container 120. In some embodiments, the second pressure may be measured via a separate pressure sensor that is positioned in fluid communication between the fluid removal valve 164 and the container 120. In some embodiments, the separate pressure sensor may be positioned or housed within the container 120.

Still referring primarily to FIG. 7A, in some embodiments the fluid removal valve 164 and the negative-pressure tube 161 may be configured so that the fluid removal valve 164 can provide a controlled flow, such as controlled flow 206, when in the closed position. For example, the fluid removal valve 164 in a closed position may allow for some amount of flow between the space in the negative-pressure tube 161 downstream of the fluid removal valve 164 and the environment external to the debridement tool 122. In some embodiments, the controlled flow 206 may correspond to a volumetric flow rate of between approximately 5 cc/min and 25 cc/min. For example, the controlled flow 206 may correspond to a flow rate of approximately 10 cc/min. A controlled flow may prevent a pressure build-up in the negative-pressure tube 161 and other components of the therapy system 100 downstream of the fluid removal valve 164, and may allow for the negative-pressure source 116 to run constantly once the debridement tool 122 has been initiated. By including a controlled flow, such as controlled flow 206, in the design of the negative-pressure tube 161 of the debridement tool 122, an operator may be able to close the fluid removal valve 164, while allowing the negative-pressure source 116 to remain running. Such a configuration may provide an operator with optimum control of the debridement tool 122. For example, an operator may wish to temporarily operate the debridement tool 122 only to deliver a fluid, such as a wound cleanser, to a tissue site, without having to deactivate or turn off the negative-pressure source 116. In other instances, the operator may wish to temporarily deactivate the negative-pressure functionality of the debridement tool 122, such as by closing the fluid removal valve 164, while the operator inspects the tissue site. The incorporation of the controlled flow feature may allow for quickly alternating between modes of operation of the debridement tool 122, without having to turn off or deactivate significant portions of the therapy system 100, such as the negative-pressure source 116.

Referring now primarily to FIG. 7B, a portion of the debridement tool 122 corresponding to that of FIG. 7A is shown, depicting a state with a fully-open fluid removal pathway, such as negative-pressure tube 161. Thus, FIG. 7B may depict the scenario where a negative-pressure source, such as negative-pressure source 116, may be activated and delivering negative pressure through the negative-pressure tube 161 to the environment external to the debridement tool 122, thereby creating a fluid removal flow 207 into the negative-pressure tube 161. Since the negative-pressure tube 161 and pressure-sensing tubes 163 are open and in fluid communication with each other, the pressure experienced within the pressure-sensing tubes 163 may be approximately equal to the pressure experienced within the negative-pressure tube 161.

Figure 8A:
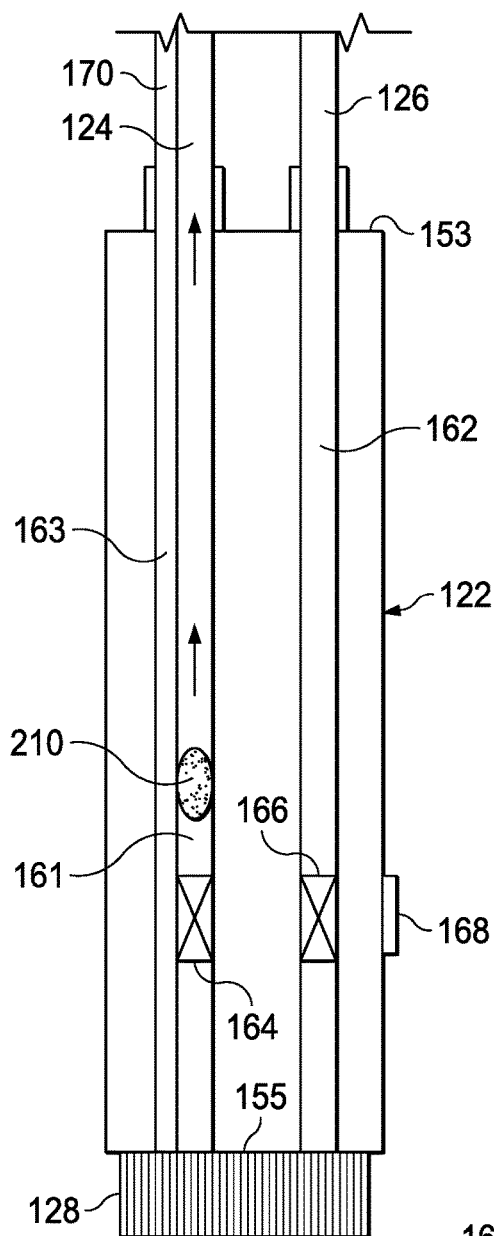
FIG. 8A is a schematic diagram illustrating a blockage condition which may be associated with some example embodiments of the therapy system of FIG. 1.

In some embodiments, the therapy system 100 may include features and functionality configured for handling a variety of fluid blockage and/or fluid leak scenarios. Referring now primarily to FIG. 8A, an embodiment of the debridement tool 122 is shown, depicting an example situation of a fluid blockage 210 in the negative-pressure tube 161 of the debridement tool 122. In accordance with the normal operation of the therapy system 100 as discussed with respect to FIGS. 3 and 4, a pump component of the negative-pressure source 116 may slowly ramp-up pump duty, with the pressure sensor 172, through the pressure-sensing tube(s) 163, being in fluid connection with and monitoring pressure at the applicator end 155 of the debridement tool 122. The negative-pressure source 116 may be set to maintain a consistent flow rate, which in some example embodiments may be approximately 1 L/min. The pump component of the negative-pressure source 116 may be allowed to continue to ramp-up to a maximum of −200 mmHg before automatically shutting down. In some embodiments, the blockage detection feature functions as the fluid removal valve 164 is not designed to fully seal, as previously described, therefore allowing for an expected controlled fluid leak of ~10 ml/min at −200 mmHg through the pressure-sensing tube(s) 163. Thus, if the therapy system 100 registers that maximum pressure (−200 mmHg) has been reached and there is no flow detected, the therapy system 100 may determine that the negative-pressure tube 161 of the debridement tool 122 is blocked.

Figure 8B:
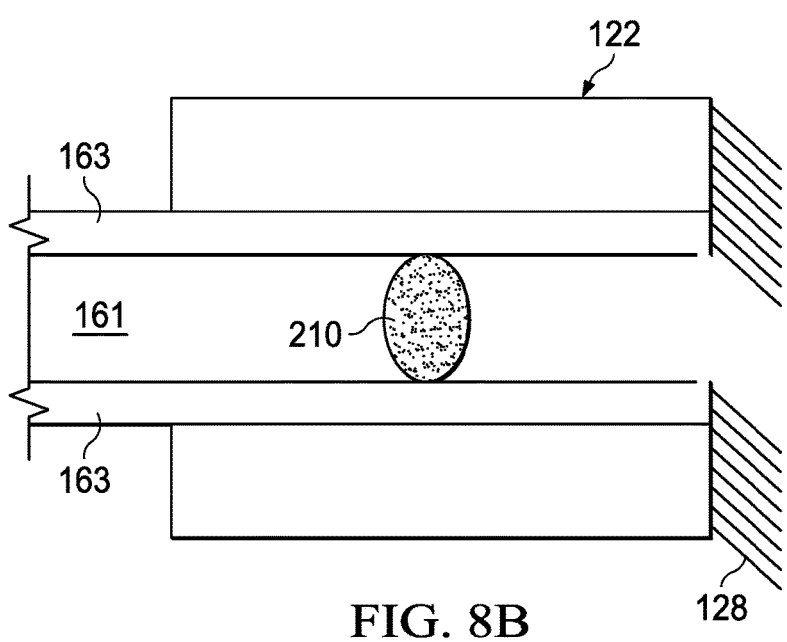
FIG. 8B is a schematic diagram showing another view of the blockage condition depicted in FIG. 8A.

Referring now also to FIG. 8B, a portion of the debridement tool 122 analogous to that of FIGS. 7A-7B is shown, including a depiction of blockage 210. According to some illustrative embodiments, in the presence of a blockage, such as blockage 210, negative pressure may increase in the negative-pressure tube 161 downstream of the blockage 210. Thus, a first pressure in the pressure-sensing tubes 163 may differ from a second pressure in the negative-pressure tube 161 downstream of the blockage 210. For example, as a result of a negative pressure increase in the negative-pressure tube 161, the absolute value of the second pressure may be greater than the absolute value of the first pressure. Based on the difference between the first pressure and the second pressure, the therapy system 100 may determine that a blockage, such as the blockage 210, exists somewhere in the fluid passageways of the therapy system 100, such as in the negative-pressure tube 161 of the debridement tool 122 or the negative-pressure conduit 124. If the pressure increase remains and the second pressure in the negative-pressure tube 161 reaches a set pressure threshold, the therapy system 100 may signal to an operator that a blockage is present. For example, the threshold pressure for alerting the operator, which may be downstream of the blockage 210 in the negative-pressure tube 161, negative-pressure conduit 124, and container 120 and measured by an additional pressure sensor which may be positioned in the container 120, may be set to a value in the range of between −150 mmHg to −400 mmHg, or in some embodiments, approximately −200 mmHg. Meanwhile, the pressure in the pressure-sensing tubes 163, which may be measured by pressure sensor 172, may be in the range of between approximately −150 mmHg to 0 mmHg. Further, the therapy system 100 may then prompt the operator to select a mode where the therapy system 100 will attempt to clear the blockage, such as the blockage 210 in the negative-pressure tube 161, by increasing the absolute value of the negative pressure provided by the negative-pressure source 116, such as to for example between −250 mmHg and −400 mmHg, or in some example embodiments approximately −300 mmHg, and operating the fluid removal valve 164 on a 10-second cycle to attempt to clear the blockage 210. Should the blockage be successfully cleared, the pressure build-up within the negative-pressure tube 161 may dissipate, and the first pressure in the pressure-sensing tubes 163 and the second pressure in the negative-pressure tube 161 may once again become approximately equal to each other. The therapy system 100 may then recognize the return of the first pressure and the second pressure to normal conditions, and may decrease the amount of negative pressure provided by the negative-pressure source 116. The therapy system 100 may then return to normal operation.

Figure 9A:
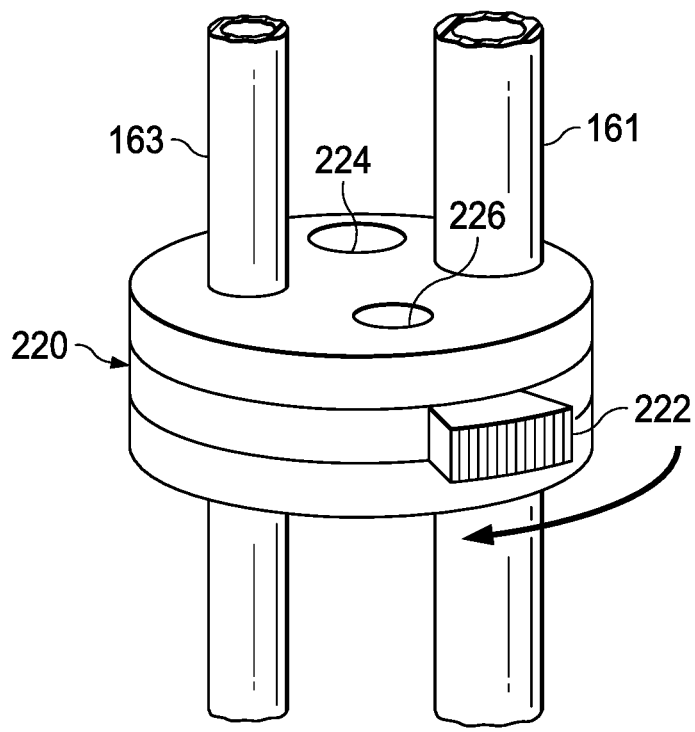
FIG. 9A is a schematic diagram illustrating additional details associated with a rotary valve, which may be associated with some example embodiments of the therapy system of FIG. 1.
Figure 9B:
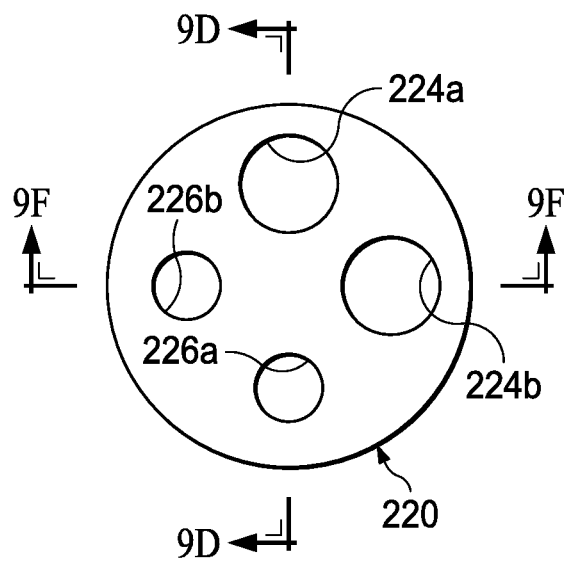
FIG. 9B is a schematic diagram illustrating additional details associated with some embodiments of the rotary valve of FIG. 9A.

FIGS. 9A-9F illustrate portions of an additional example embodiment of the debridement tool 122, which may allow for alternative pressure-sensing features of the therapy system 100. For example, the passageways of the debridement tool 122 may be arranged to allow for different aspects of pressure-sensing and control functionality using a rotary valve system. Referring to FIG. 9A, additional details associated with a rotary valve 220 are shown. For example, the rotary valve 220 may include a dial 222 configured for allowing an operator to adjust the position of the rotary valve 220. Referring also to FIG. 9B, the rotary valve 220 may include passageways for negative-pressure delivery, such as a first negative-pressure opening 224a and a second negative-pressure opening 224b, and passageways for enabling pressure sensing, such as a first pressure-sensing opening 226a and a second pressure-sensing opening 226b.

The rotary valve 220 may be configured to allow for switching between activation and deactivation of the delivery of negative pressure to the applicator end 155 of the debridement tool 122. For example, referring now primarily to FIG. 9C, to perform fluid removal from the tissue site 102, the rotary valve 220 may be placed in a first position so that both the negative-pressure tube 161 and the pressure-sensing tube 163 are placed in fluid communication with the applicator end 155 of the debridement tool 122 and the environment external to the debridement tool 122. Referring now also to FIG. 9D, a cross-section view of the rotary valve 220 according to the line 9D-9D of FIG. 9B is shown. As shown in FIGS. 9C and 9D, the rotary valve 220 may include a first negative-pressure opening 224a and a first pressure-sensing opening 226a. The first negative-pressure opening 224a may provide an opening for maintaining a continuous fluid path through portions of the negative-pressure tube 161, while the first pressure-sensing opening 226a may provide an opening for maintaining a continuous path through the portions of the pressure-sensing tube 163.

Referring now primarily to FIG. 9E, the rotary valve 220 may be placed in a second position to stop fluid removal from the tissue site 102. In the second position, the rotary valve 220 may place the pressure-sensing tube 163 in fluid communication with the negative-pressure tube 161 through pressure return passageway 228 of the rotary valve 220. Referring now also to FIG. 9F, a cross-section view of the rotary valve 220 according to the line 9F-9F of FIG. 9B is shown. As shown in FIGS. 9E and 9F, the second negative-pressure opening 224b and the second pressure-sensing opening 226b may be fluidly connected by a pressure return passageway 228. In some embodiments, the rotary valve 220 can be closed as depicted in FIGS. 9E and 9F to place the negative-pressure tube 161 in fluid communication with the pressure-sensing tube 163. Closing the rotary valve 220 may also fluidly couple the negative-pressure tube 161 to the pressure-sensing lumen 170 and the pressure sensor 172 of FIG. 3, via the pressure-sensing tube 163. Pressure measurements may be determined for different portions of the fluid passageways of the debridement tool 122 and therapy system 100 based on changing the position of the rotary valve 220.

In operation, when the fluid removal functionality is required, an operator may operate the dial 222 of the rotary valve 220 to set the rotary valve 220 to the first position, which may align the first negative-pressure opening 224a with the two different sections of the negative-pressure tube 161 on the two sides of the rotary valve 220. The section of the negative-pressure tube 161 downstream of the rotary valve 220, which may also be in fluid communication with the negative-pressure conduit 124 and the negative-pressure source 116, may be placed in fluid communication with the environment external to the debridement tool 122. In this first position, the first pressure-sensing opening 226a may also be aligned with the two different sections of the pressure-sensing tube 163, also placing the portion of the pressure-sensing tube 163 on the same side of the rotary valve 220 as the pressure-sensing lumen 170 and pressure sensor 172, in fluid communication with the environment external to the debridement tool 122. In some embodiments, the movement of the rotary valve 220 to place the pressure sensor 172 in fluid communication with the external environment through the pressure-sensing tube 163 may indicate to the control system of the therapy system 100 that the operator requires fluid removal.

Once the negative-pressure tube 161 and the pressure-sensing tube 163 are open to fluid communication with the environment external to the debridement tool 122, the therapy system 100 may then try to drive the pressure in the container 120 to maintain a predetermined pressure, such as −200 mmHg, and deliver negative pressure through the negative-pressure tube 161 to the applicator end 155 of the debridement tool 122. The pressure sensor 172 in fluid communication with the pressure-sensing tube 163 may then monitor the pressure at the applicator end 155 of the debridement tool 122. The pressure sensor 172, through the pressure-sensing tube 163, may sense atmospheric pressure at the applicator end 155, and the negative-pressure source 116 may run to attempt to cause the pressure sensor 172 to reach the predetermined pressure at the applicator end 155. However, the negative-pressure source 116 may be unable to reach the predetermined pressure level, as the negative-pressure tube 161 and the pressure-sensing tube 163 may remain open to the atmosphere, and the negative-pressure source 116 may continue to run to maintain a flow through the negative-pressure tube 161. In some embodiments, if the therapy system 100 has to continually increase the workload of the negative-pressure source 116 in order to maintain the pressure at the applicator end 155 detected by the pressure sensor 172 through the pressure-sensing tube 163, or is unable to maintain pressure during operation, the therapy system 100 may interpret this condition to be the presence of a blockage, such as a blockage within the negative-pressure tube 161. The therapy system 100 may then give the operator an option to attempt to clear the fluid passageways, such as the negative-pressure tube 161, of the therapy system 100. This may be achieved by increasing the negative pressure provided by the negative-pressure source 116 up to a set pressure, which may be approximately −300 mmHg, at set intervals, which may be approximately 10 seconds, until the blockage has been cleared.

In contrast, if fluid removal is not desired, the operator may once again use the dial 222 to set the rotary valve 220 to the second position, which may align the second negative-pressure opening 224b with the two different sections of the negative-pressure tube 161 and align the second pressure-sensing opening 226b with the two different sections of the pressure-sensing tube 163. In this configuration, the negative-pressure tube 161 and the pressure-sensing tube 163 may be placed in direct fluid communication with each other through the pressure return passageway 228, as shown in FIGS. 9E and 9F. When the rotary valve 220 is placed in the second position, the negative-pressure tube 161 and the pressure-sensing tube 163 may be closed off from fluid communication with the tissue site 102 and external environment. In some embodiments, as the pressure within the closed environment, including the negative-pressure source 116 and the pressure sensor 172, reaches a predetermined level, for example −200 mmHg, the therapy system 100 may determine that fluid removal is no longer required. In such instances, the negative-pressure source 116 may reduce output, or in some cases, cease operation.

Figure 10A:
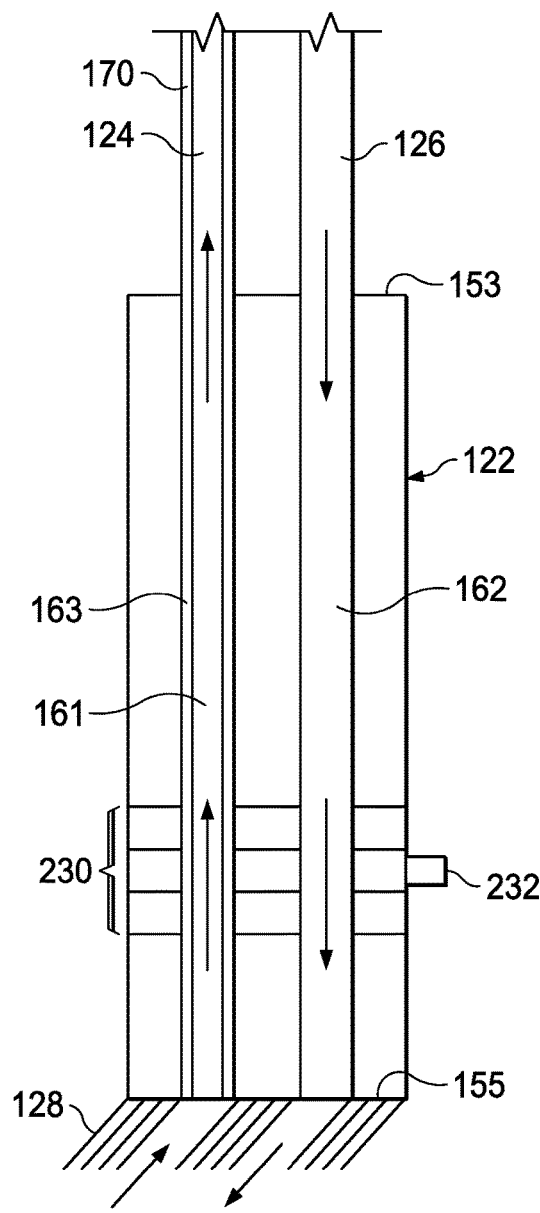
FIG. 10A is a schematic diagram illustrating additional details that may be associated with some example embodiments of the debridement tool of FIG. 1, including a rotary valve.
Figure 10B:
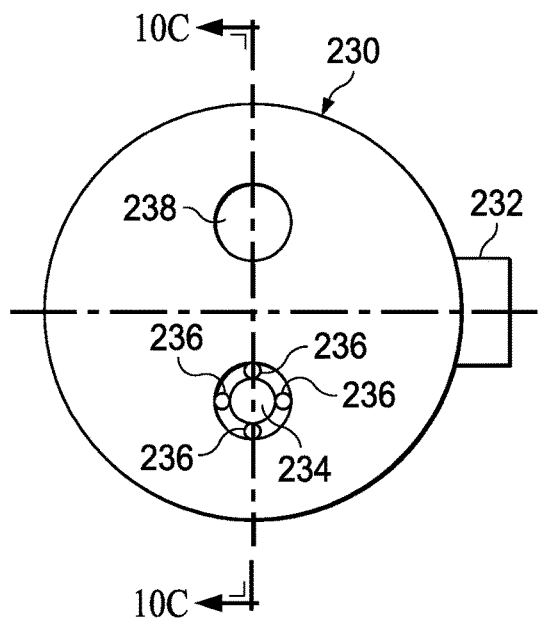
FIG. 10B is a schematic diagram illustrating additional details associated with some embodiments of the debridement tool and rotary valve of FIG. 10A.
Figure 10C:
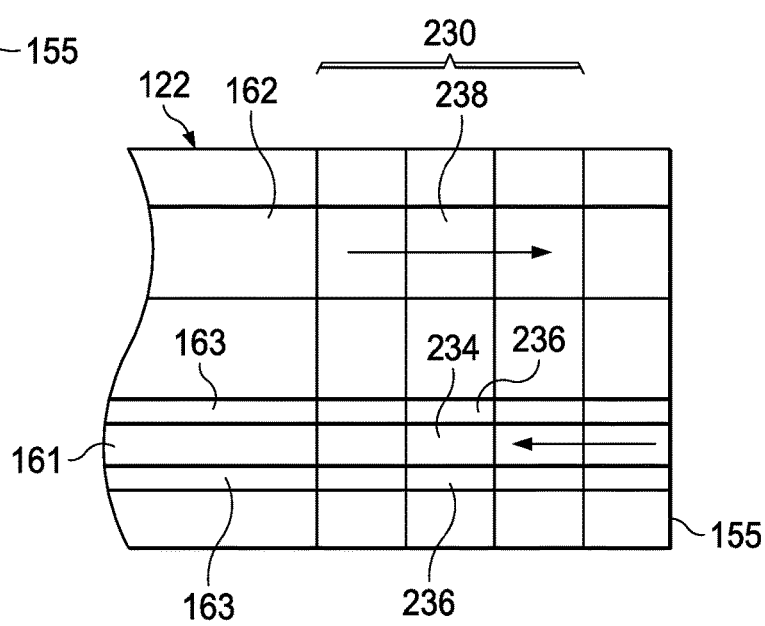
FIG. 10C is a cross-section view of a portion of the debridement tool and rotary valve of FIG. 10B.

Referring now to FIGS. 10-12, collectively, portions of an additional example embodiment of the debridement tool 122 are shown, illustrating certain pressure-sensing features and functionality that may be associated with some embodiments. More specifically, the embodiment of the debridement tool 122 shown in FIGS. 10-12 may include another embodiment of a rotary valve system. Referring now to FIG. 10A, details associated with the rotary valve 230 are shown. For example, the rotary valve 230 may include a dial 232 for allowing an operator to adjust the position of the rotary valve 230 with respect to the fluid passageways of the debridement tool 122. Referring also to FIG. 10B, the rotary valve 230 may include a passageway for negative-pressure delivery, collectively negative-pressure opening 234. The rotary valve 230 may also include one or more passageways for enabling pressure sensing, collectively pressure-sensing opening(s) 236. For example, in the example embodiment of FIGS. 10A-10C, four pressure-sensing openings 236a, 236b, 236c, and 236d, are positioned and spaced around the circumference of the negative-pressure opening 234. Each of the four pressure-sensing openings 236a-236d may correspond and be placed in fluid communication with a single pressure-sensing tube 163. Thus, in the embodiment of FIGS. 10A-10C, the debridement tool 122 may include four pressure-sensing tubes 163 spaced around the circumference of the negative-pressure tube 161. Furthermore, the rotary valve 230 may include a passageway for fluid delivery, such as fluid-delivery opening 238.

As discussed with respect to the rotary valve 220 of FIGS. 9A-9F, the rotary valve 230 of FIGS. 10A-10C similarly may be configured to allow for switching between activation and deactivation of the delivery of negative pressure to the applicator end 155 of the debridement tool 122. Additionally, the rotary valve 230 may also be capable of activating and deactivating fluid delivery from a fluid source of the therapy system 100, such as fluid source 118. For example, referring now also to FIG. 10C, a cross-section view of a portion of the debridement tool 122 according to the line 10C-10C of FIG. 10B is shown. As shown in FIG. 10C, when it is desirable to administer negative pressure as well as fluid delivery to a tissue site, such as tissue site 102, the rotary valve 230 may be placed in an open position so that both the negative-pressure tube 161 and the pressure-sensing tubes 163 are placed in fluid communication with the applicator end 155 of the debridement tool 122 and the environment external to the debridement tool 122 at the tissue site 102. As shown in FIG. 10C, the negative-pressure opening 234 may provide a continuous fluid path between portions of the negative-pressure tube 161, while the pressure-sensing openings 236 may provide passageways between portions of the pressure-sensing tubes 163 on either side of the rotary valve 230. Additionally, the fluid-delivery opening 238 may provide a passageway for delivering fluid through the rotary valve 230. If the rotary valve 230 is in the open position, the fluid source 118 may be configured or set to deliver fluid through the fluid-delivery tube 162.

Still referring primarily to FIG. 10C, the rotary valve 230 may allow for collecting and comparing pressure measurements at different portions of the debridement tool 122. For example, a first pressure may be a pressure within at least one of the pressure-sensing tubes 163 and may be determined by a pressure sensor that is connected to at least one of the pressure-sensing tubes 163. In some embodiments, all of the pressure-sensing tubes 163 may be in fluid communication with a single pressure sensor, such as pressure sensor 172, while in other embodiments, each of the pressure-sensing tubes 163 may be in fluid communication with a separate pressure sensor. A second pressure may refer to a pressure within the negative-pressure tube 161, and more specifically, the pressure downstream from the negative-pressure opening 234 of the rotary valve 230. The second pressure may correspond to a pressure within a container or canister, such as container 120. In some embodiments, the second pressure may be measured by the negative-pressure source 116 itself or by an additional pressure sensor that is in fluid communication with the negative-pressure tube 161 and positioned between the rotary valve 230 and the negative-pressure source 116, for example in the container 120. When the fluid pathways of the debridement tool 122, including the negative-pressure tube 161 and the pressure-sensing tubes 163, are open and in fluid communication with each other, the pressure within the pressure-sensing tubes 163, or the first pressure, may be approximately equal to the pressure within the negative-pressure tube 161, or the second pressure.

Figure 11A:
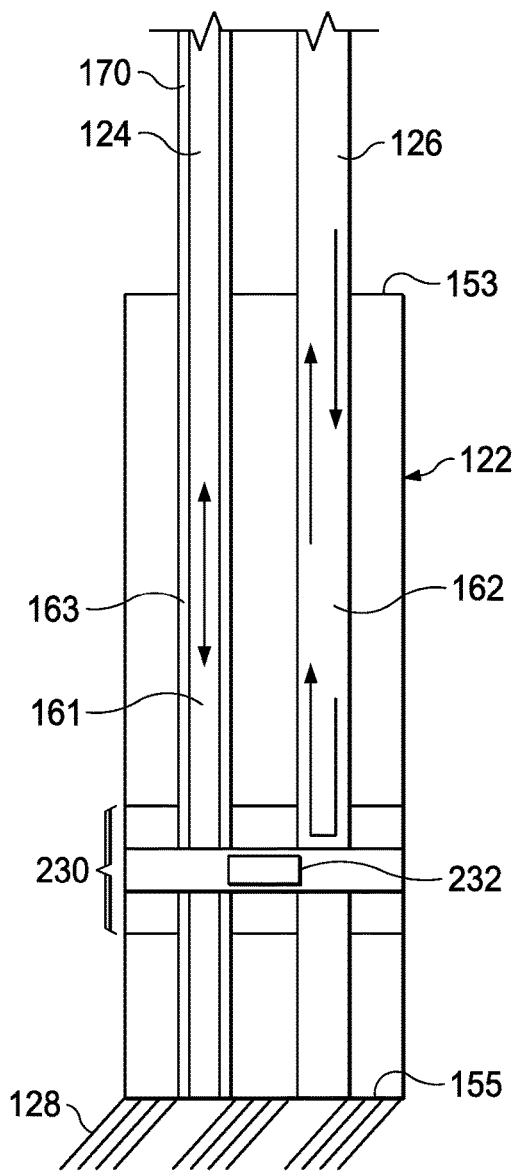
FIG. 11A is a schematic diagram illustrating additional details that may be associated with some example embodiments of the debridement tool of FIG. 1, including a rotary valve.
Figure 11B:
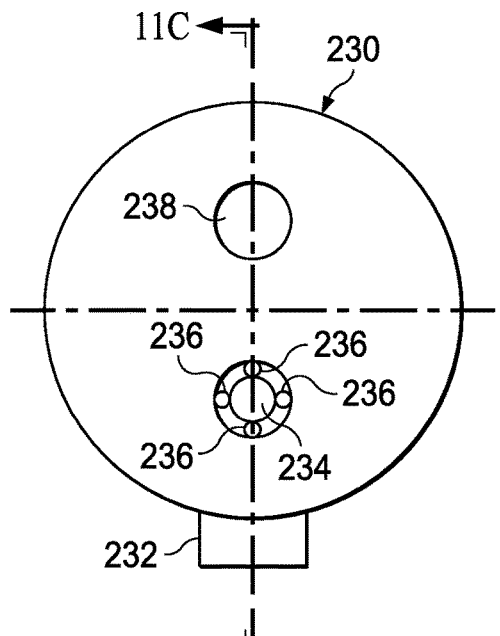
FIG. 11B is a schematic diagram illustrating additional details associated with some embodiments of the debridement tool and rotary valve of FIG. 11A.
Figure 11C:
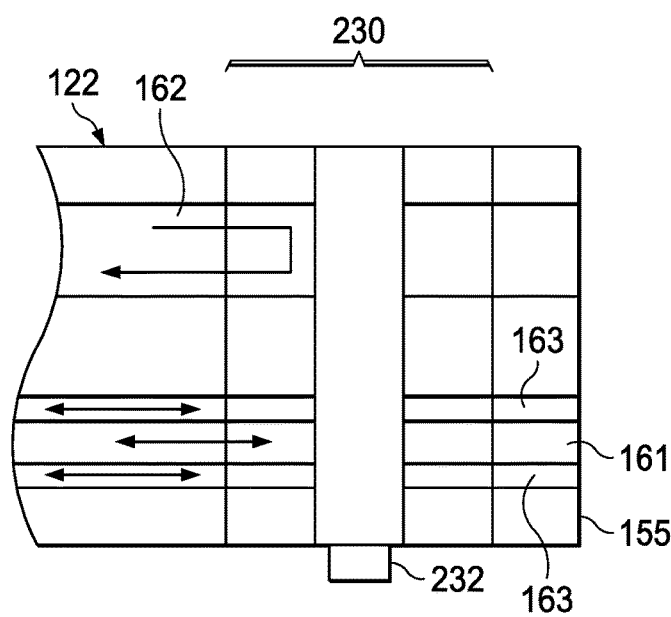
FIG. 11C is a cross-section view of a portion of the debridement tool and rotary valve of FIG. 11B.

Referring now to FIGS. 11A-11C, the debridement tool 122 is shown with the rotary valve 230 in a closed position. In this closed position, the rotary valve 230 may substantially obstruct the fluid communication between a downstream side of the negative-pressure tube 161, or space between the rotary valve 230 and the negative-pressure source 116, and an environment exterior to the debridement tool 122. The rotary valve 230 may also substantially obstruct fluid communication through the pressure-sensing tubes 163 and the fluid removal tube 162. Pressure within the various passageways of the debridement tool 122 may be measured at two different points. A first pressure may refer to a pressure within at least one of the pressure-sensing tubes 163 and may be determined by a pressure sensor that is fluidly connected to the pressure-sensing tubes 163, such as pressure sensor 172. A second pressure may refer to a pressure within the negative-pressure tube 161, and more specifically the pressure downstream from the rotary valve 230. Thus, the second pressure may refer to a pressure experienced within the container 120, and the second pressure may be measured by an additional pressure sensor that is in fluid communication with the negative-pressure tube 161 and positioned between the rotary valve 230 and the negative-pressure source 116, for example in the container 120. Since the rotary valve 230, when in the closed position, closes the negative-pressure tube 161 from the external environment, the absolute value of the negative pressure within the negative-pressure tube 161 and container 120 will increase as the negative-pressure source 116 is left in an "on" state. In some embodiments, the rotary valve 230, when in the closed position, can allow the pressure-sensing tubes 163 to remain in fluid communication with the negative-pressure tube 161. In such instances, the first pressure may be approximately equal to the second pressure, and both the first pressure and the second pressure may correspondingly increase or decrease.

In some embodiments, the therapy unit 114 may be configured to determine when the first pressure and the second pressure both approximately reach a set threshold pressure, such as for example, approximately −200 mmHg. The therapy unit 114 may be programmed to determine that since the first pressure and the second pressure are equal, the rotary valve 230 must be positioned in the closed position and fluid removal is not needed. The therapy unit 114 may not signal an alarm, despite the second pressure increasing to the set threshold, since the first pressure approximately matches the second pressure. The therapy unit 114 may thus assume that no blockage is present in fluid passageways of the debridement tool 122. The rotary valve 230 may also close off the fluid-delivery tube 162 from the environment external to the debridement tool 122. The fluid source 118 may sense an absence of fluid flow, and the therapy unit 114 may signal the fluid source 118 to slow the fluid delivery rate down to a slower rate. If the fluid-delivery tube 162 is no longer closed off by the rotary valve 230, an increasing flow rate may be detected by the fluid source 118 and therapy unit 114, and the fluid source 118 may transition to a greater fluid delivery rate.

Figure 12A:
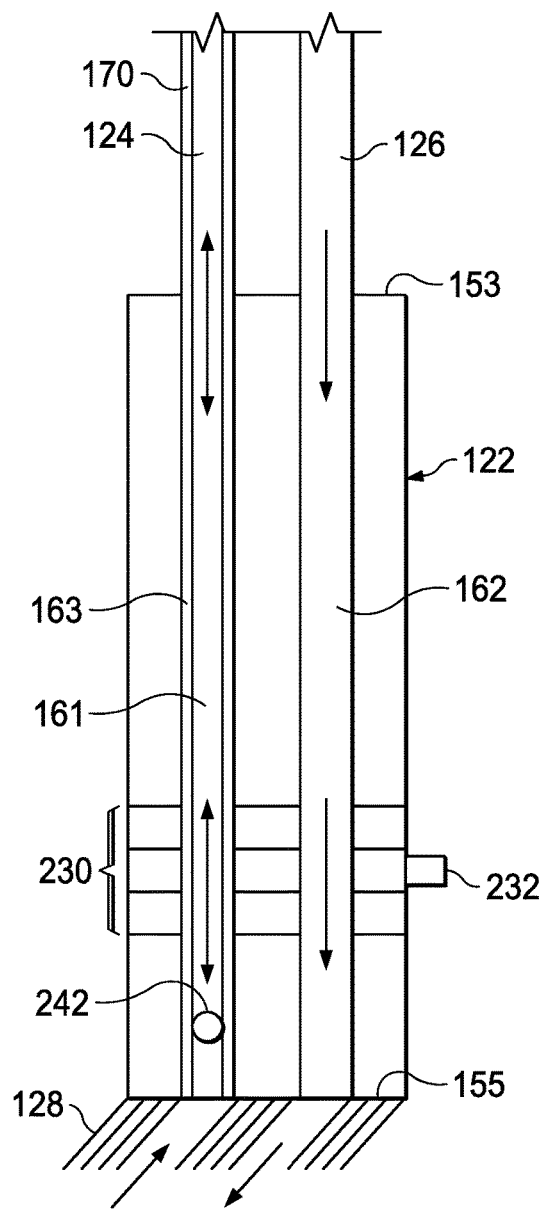
FIG. 12A is a schematic diagram illustrating additional details that may be associated with some example embodiments of the debridement tool of FIG. 1, including a rotary valve, in conjunction with a blockage condition.
Figure 12B:
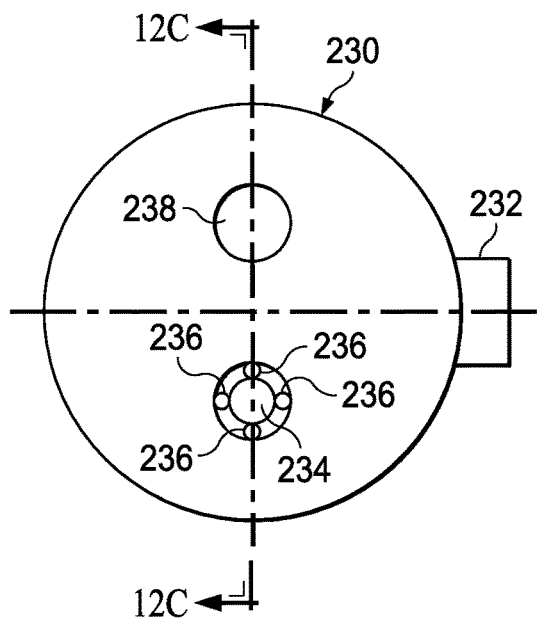
FIG. 12B is a schematic diagram illustrating additional details associated with some embodiments of the debridement tool and rotary valve of FIG. 12A.
Figure 12C:
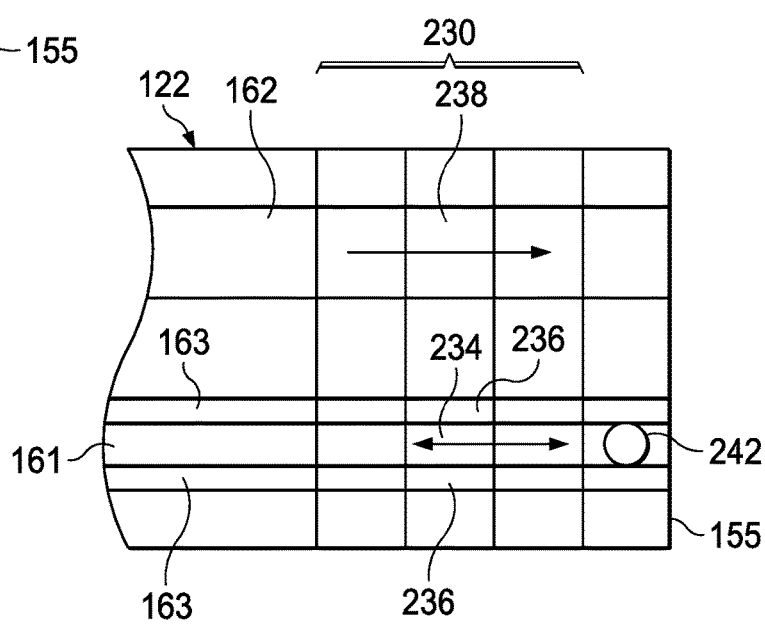
FIG. 12C is a cross-section view of a portion of the debridement tool and rotary valve of FIG. 12B.

Referring now to FIGS. 12A-12C, the debridement tool 122 is shown with the rotary valve 230 again positioned in an open position, however an example situation of a fluid blockage 242 in the negative-pressure tube 161 of the debridement tool 122 is shown. In the scenario depicted in FIGS. 12A-12C, the rotary valve 230 is placed in the open position, thus allowing fluid communication of the negative-pressure tube 161, fluid delivery tube 162, and the one or more pressure-sensing tubes 163 with an environment external to the debridement tool 122. In the situation of the fluid blockage 242, the therapy unit 114 may detect an increase in negative pressure that occurs within the negative-pressure tube 161 downstream of the blockage 242. The therapy unit 114 may then detect a pressure difference between a first pressure measured from within the pressure-sensing tubes 163 and a second pressure measured from within the negative-pressure tube 161 downstream of the blockage 242. For example, the second pressure downstream of the blockage 242 may have a greater absolute value than the first pressure within the one or more pressure-sensing tubes 163. Based on the difference between the first pressure and the second pressure, the therapy unit 114 may determine that the blockage 242 exists in the negative-pressure tube 161. The therapy unit 114 may then subsequently prompt an operator to attempt to clear the blockage, which may be achieved by increasing the negative-pressure delivered by the negative-pressure source 116 to a set level, such as, for example, approximately −300 mmHg. However, despite the presence of blockage 242, the fluid-delivery tube 162 may remain open, through the fluid-delivery opening 238 of the rotary valve 230, to the external environment, including tissue site 102, and thus fluid may be continue to be delivered to the tissue site 102.

In addition to the embodiments of the debridement tool 122 which may include various versions of a rotary valve, embodiments of the debridement tool 122 may additionally or alternatively include rotary valves with different combinations of fluid openings and passageways. For example, in some embodiments, a rotary valve for allowing fluid removal, but no simultaneous fluid delivery, or vice versa, could be provided.

FIGS. 13-15 collectively provide images related to testing of some features associated with some example embodiments of the debridement tool 122 and the therapy system 100. The images show results of testing eschar models created by branding pork chops with a heated steel rod. Branding of each sample was performed for between 30-60 seconds, however level of eschar was based on visual inspection. Testing of the debridement tool 122 and the therapy system 100 was conducted at a uniform time of 3 minutes for each tested embodiment of the debridement tool 122. During the testing procedures, negative pressure and fluid flow were provided by a V.A.C.ULTA™ Unit, with fluid pump settings of approximately 35% pump duty of 1.6 mL/sec flow rate.

Figure 13A:
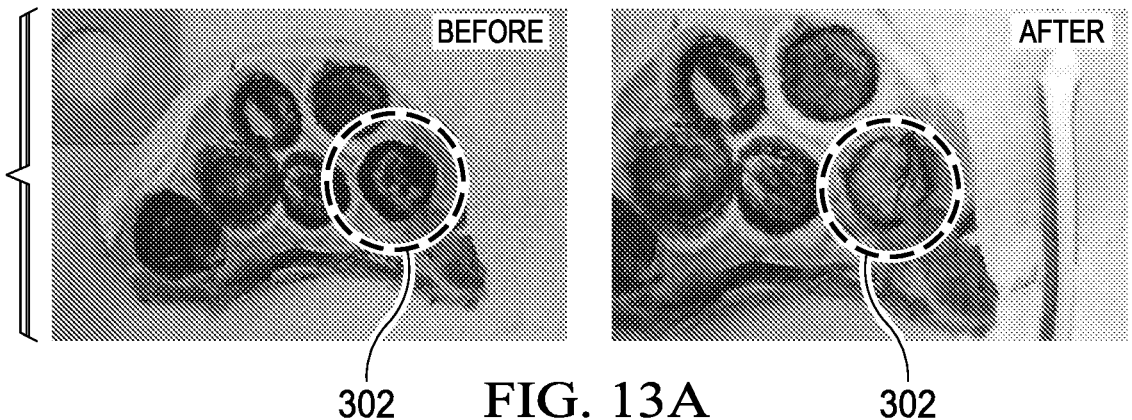
FIGS. 13A-13C are perspective top views showing before and after views of sample test materials used to simulate various tissue sites.

FIG. 13 collectively provides views of an eschar model before and after being debrided with an exemplary debridement tool having a brush head with firm bristles. More specifically, FIG. 13A shows before-and-after views of an eschar model debrided without fluid delivery or the application of negative-pressure therapy. Comparing sample area 302 before and after debridement illustrates that the debridement procedure removed a majority of dark eschar and removed some central necrotic tissue.

Figure 13B:
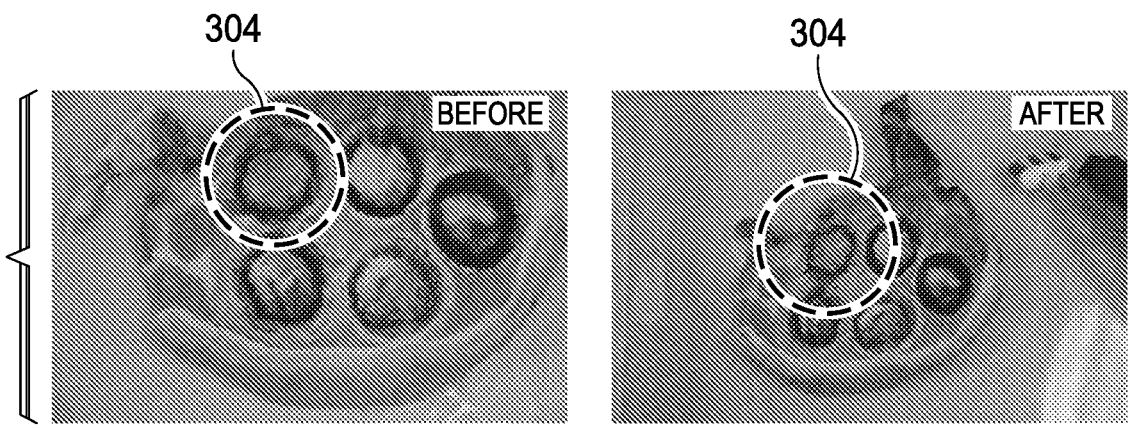

FIG. 13B includes images of an eschar model before and after being debrided with continuous fluid delivery and negative-pressure. Comparing the sample area 304 illustrates that the debridement procedure removed a significant portion of the dark eschar, and an outer ring of black eschar remained in place. Additionally, the procedure did remove the necrotic tissue central to the sample area 304.

Figure 13C:
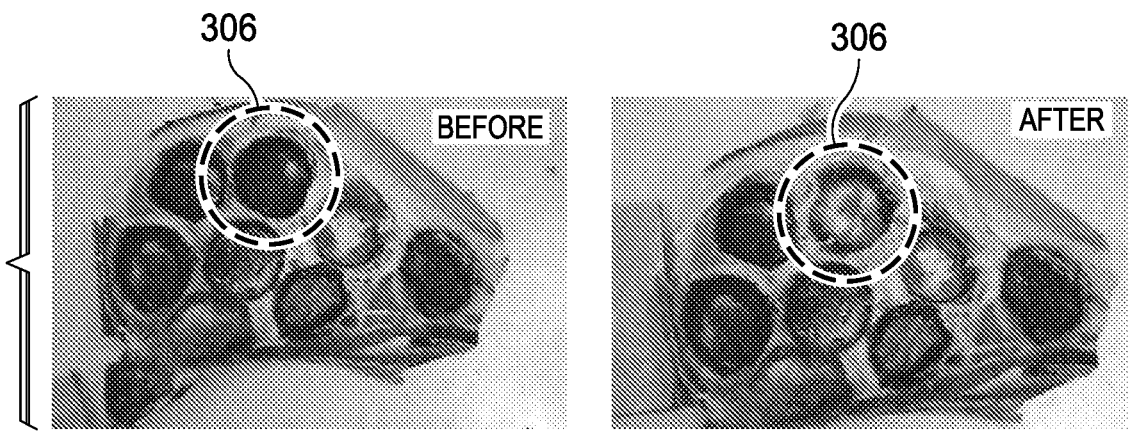

FIG. 13C includes images of an eschar model before and after being debrided with continuous fluid delivery, negative-pressure applied, and vibration/oscillation functionality. A comparison of sample area 306 shows that the dark eschar was thoroughly removed, as well as was some of the central necrotic tissue. Observations indicated that the vibration feature was beneficial to both fluid removal and cleaning of the sample site.

Figure 14A:
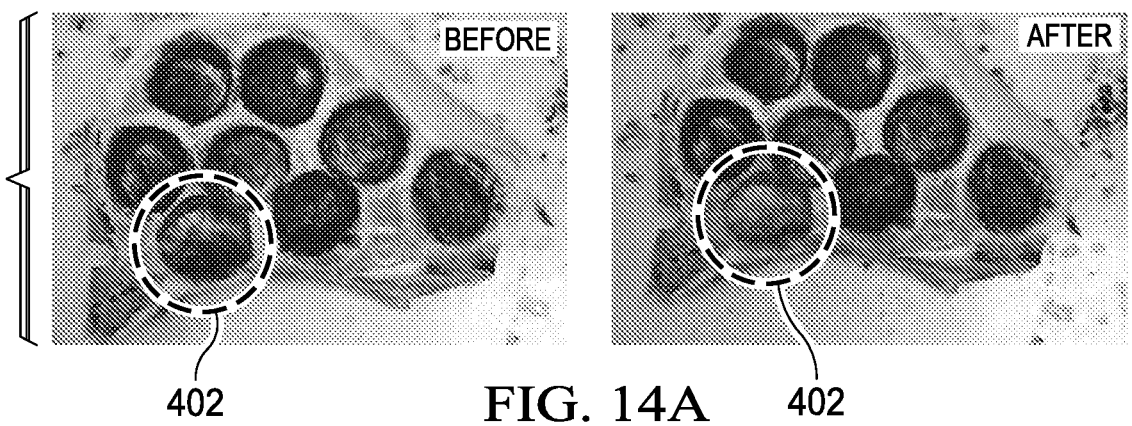
FIGS. 14A-14C are perspective top views showing before and after views of sample test materials used to simulate various tissue sites.

FIG. 14 collectively includes images of an eschar model before and after being debrided with an exemplary debridement tool having a brush head with soft bristles. FIG. 14A includes images of the eschar model before and after being debrided without fluid delivery or negative pressure. Comparing sample area 402 illustrates that the debridement procedure removed a majority of dark eschar, and some amount of necrotic tissue.

Figure 14B:
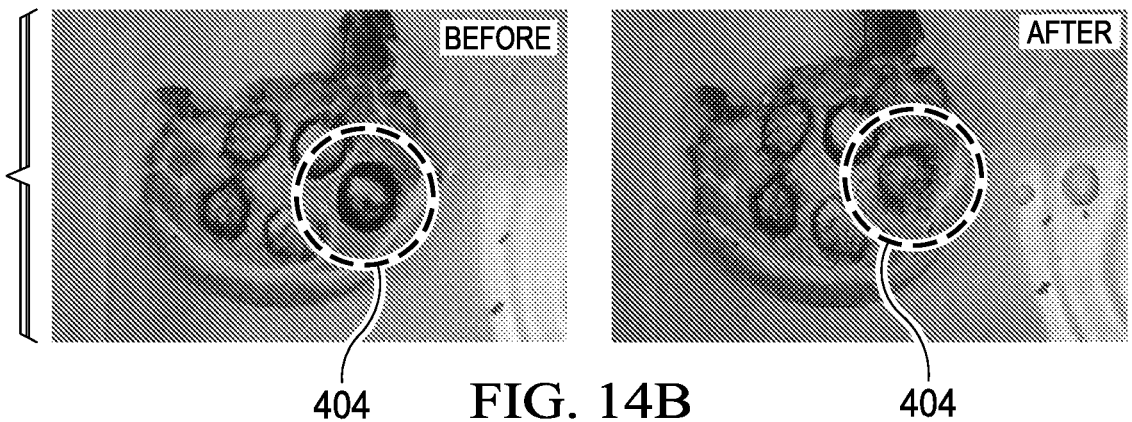

FIG. 14B includes images of an eschar model before and after being debrided with continuous fluid delivery and negative pressure. Comparing sample area 404 illustrates that the debridement procedure removed the majority of the black eschar. Additionally, the procedure did remove necrotic tissue in areas of the sample area 404.

Figure 14C:
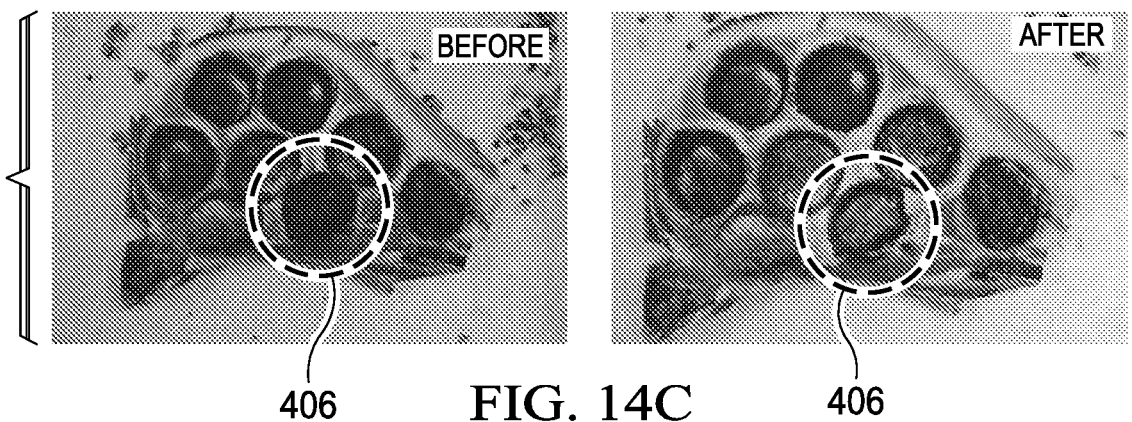

FIG. 14C includes images of an eschar model before and after being debrided with continuous fluid delivery, negative pressure applied, and vibration/oscillation functionality. Comparing the sample area 406 illustrates that the debridement procedure thoroughly removed the dark eschar. Some necrotic tissue was removed from the sample site. The inclusion of the vibration functionality may benefit the operator by requiring significantly less pressure to be applied to the debridement tool 122. Additionally, the configuration of the debridement tool 122 tested with respect to the results shown in FIG. 14C may offer particular benefits for wounds with high levels of exudate and slough, as opposed to dark eschar. For example, less user effort and amount of downward pressure applied may reduce the spreading or scattering around of exudates.

Figure 15A:
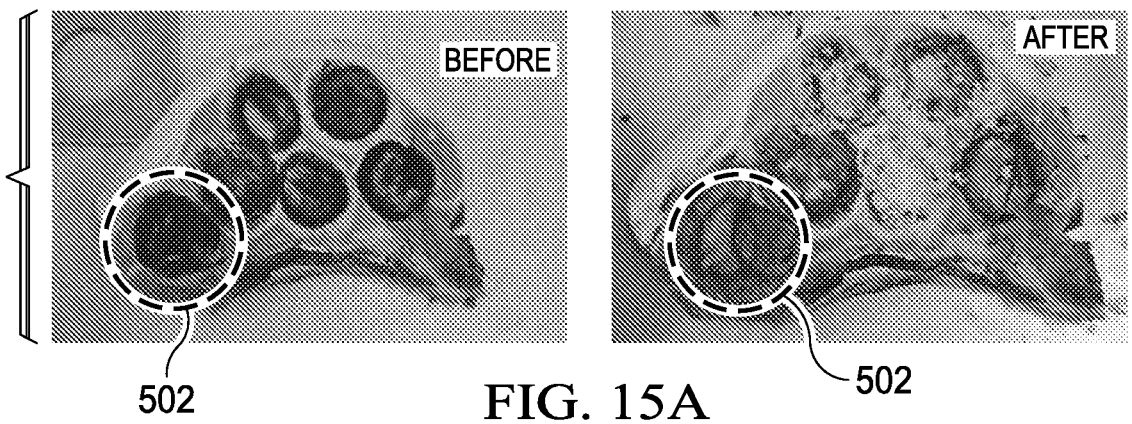
FIGS. 15A-15C are perspective top views showing before and after views of sample test materials used to simulate various tissue sites.

FIG. 15 collectively includes images of an eschar model before and after being debrided with an exemplary debridement tool having a brush head with hard bristles. FIG. 15A includes images of the eschar model before and after being debrided without fluid delivery or negative pressure. Comparing sample area 502 illustrates that the debridement procedure removed a majority of dark eschar and a portion of the necrotic tissue.

Figure 15B:
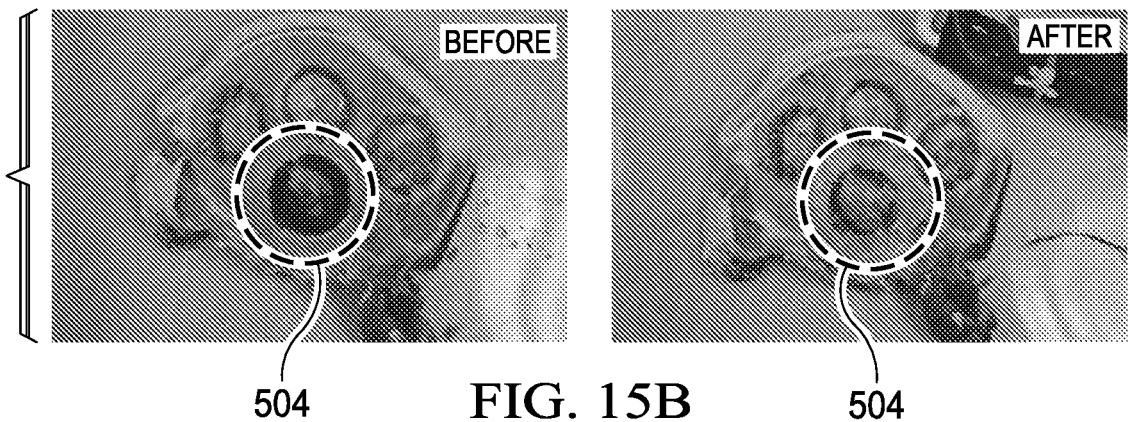

FIG. 15B includes images of an eschar model before and after being debrided with continuous fluid delivery and negative pressure. Comparing the sample area 504 illustrates that the debridement procedure removed the majority of the dark eschar, with the exception of some of the deeper, outer eschar. Additionally, the majority of the necrotic tissue central to the sample area 504 was removed. The procedure did involve some scraping of the sample area 504.

Figure 15C:
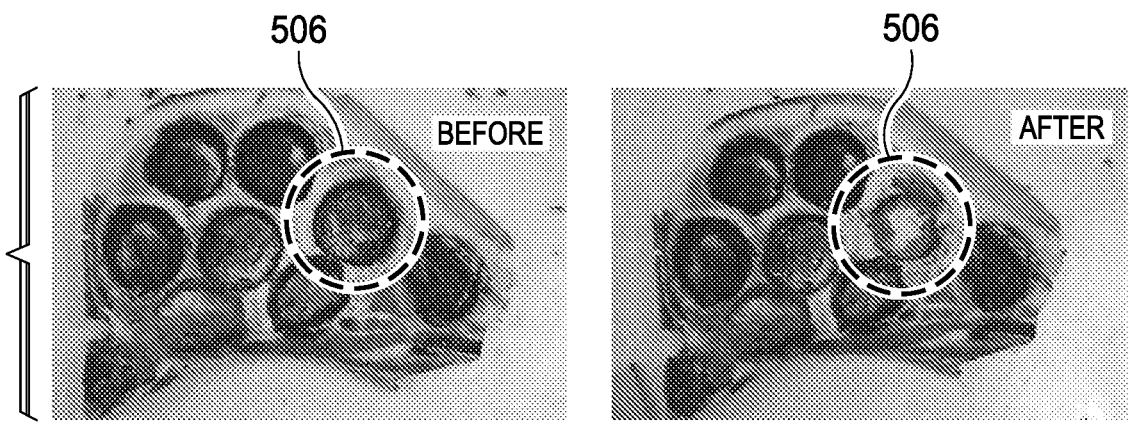

FIG. 15C includes images of an eschar model before and after being debrided with continuous fluid delivery, negative pressure applied, and vibration/oscillation functionality. Comparing the sample area 506 illustrates that the debridement procedure thoroughly removed the majority of the dark eschar, however some of the deeper eschar still remained. Additionally, the majority of the necrotic tissue located in the center of the sample area 506 was also removed. The inclusion of the vibration functionality resulted in less effort required by the operator. The vibration feature benefited both fluid removal as well as cleaning of the sample area 506, particularly in areas with hard eschar. Researchers noted that the configuration of using hard bristles with continuous fluid delivery, negative-pressure application, and vibration functionality provided the best debridement results.

Several conclusions were gathered from the debridement tests associated with FIGS. 13-15. First, the bristle lengths and diameters may be varied to achieve better cleaning performance of wounds. For example, soft bristles may be utilized to clean more delicate and sensitive wounds, and may also be effective for treating wounds with high levels of slough. Firm bristles may also be used to clean wounds with high levels of slough and exudate, and may also be effective against some levels of hard eschar and necrotic tissue. Hard bristles may be used to clean wounds with dark, hard eschar without requiring significant user effort. Second, incorporating vibration/oscillation functionality may provide several advantages. In addition to improving the results of the debridement process, the vibration feature may also assist with the fluid removal process. The vibration feature may also offer significant reductions in the amount of user effort required to perform the debridement procedures.

The systems, apparatuses, and methods described herein may provide significant advantages. For example, a therapy system described above, such as therapy system 100, may provide a low-pain, efficient solution for providing an alternative form of debridement therapy. The therapy system 100 may also enable debridement procedures to be performed at the bedside of patients by a skilled nurse or caregiver, rather than requiring a surgical environment and associated team. As such, powered negative-pressure wound therapy systems may be enhanced to provide a simple and effective handheld wound cleaning and debridement device. The therapy system 100 may provide controlled fluid delivery and fluid removal, which may soften necrotic tissue, irrigate the wound site, and facilitate cleaning and the removal of unwanted particulates. Furthermore, the flow created by a negative-pressure supply, such as the negative-pressure source 116, may be used to remove fluids and debrided particulates from the wound site. Additionally, some embodiments of the debridement tool 122 may provide oscillation or vibration, which can reduce the amount of user effort required to perform the debridement procedure, help loosen necrotic tissue, assist with the removal of fluid and debridement particles, and reduce overall treatment time. All system elements may be independently controlled by the operator in some embodiments, including those related to cleansing the wound site in addition to negative-pressure therapy.

By providing an easy-to-control debridement tool offering powered assistance, caregivers who may not be trained and/or confident with mechanical debridement techniques requiring sharp instruments may successfully perform a greater number of debridement procedures, often avoiding the need for surgical procedures to be conducted. As a result, not only can patient waiting times likely be reduced, but surgeon time and surgical environments may also be relieved and made available for other treatments and procedures. Additionally, by utilizing existing negative-pressure wound therapy systems in the debridement process, wound cleaning and debridement may be conducted at a patient's bedside before a wound is redressed and then subjected to negative-pressure wound therapy by the same base unit. The therapy system 100 may also be effective in the surgical environment.

Other possible relevant areas of use for the systems and debridement tools disclosed herein may include dental applications. For example, the disclosed debridement tools may be used to aid dental cleaning, such as to facilitate the removal of plaque and calculus, as well as for dental debridement procedures.

Additionally, some embodiments of the debridement tool 122 may be designed as a single-use, disposable unit, which can further increase ease and efficiency of debridement procedures for clinicians. The debridement tool 122 may also include built-in features for clearly signaling to users that the device is not to be reused. For example, the tubing connectors of the debridement tool 122 for connecting to the conduits of the therapy system 100 may be designed to have a melting point below temperatures reached during autoclaving and steam sterilization, which can prevent use following sterilization procedures. Additionally, the debridement tool 122 may include one or more features that are designed to be triggered, which may also prevent reuse. One example is a deformable piece as part of the tubing connectors of the debridement tool 122 that may snap and prevent reuse during connection to the conduits of the therapy system 100. Furthermore, cautions against reuse can be provided by labeling additions and other warnings on the debridement tool 122, as well as packaging.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the debridement tool 122, the container 120, or both may be eliminated or separated from other components for manufacture or sale. In other example configurations, the therapy unit 114 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for treating a tissue site, comprising:
   a debridement tool having a first end and a second end and comprising:
      a first fluid conduit extending from the first end to the second end,
      a second fluid conduit extending from the first end to the second end,
      a brush attached to the second end:
   a negative-pressure source adapted to be fluidly coupled to the first fluid conduit at the first end of the debridement tool;
   a fluid source adapted to be fluidly coupled to the second fluid conduit at the first end of the debridement tool; and
   a control unit configured to interface with an operator for receiving and displaying operation parameters of the negative-pressure source and the fluid source.

2. The system of claim 1, wherein the debridement tool further comprises a switch positioned on an external surface and configured to allow an operator to control delivery of a fluid from the fluid source.

3. The system of claim 1, wherein the debridement tool further comprises:
   a first switch configured to activate and deactivate the fluid source; and
   a second switch configured to activate and deactivate the negative-pressure source.

4. The system of claim 1, wherein the first fluid conduit comprises a first valve adapted to restrict delivery of negative pressure to the second end of the debridement tool.

5. The system of claim 4, wherein the first valve is further adapted to permit a predetermined, controlled fluid leak.

6. The system of claim 1, wherein the second fluid conduit comprises a second valve adapted to control delivery of a fluid from the fluid source.

7. The system of claim 1, further comprising:
   a negative-pressure delivery conduit adapted to fluidly connect the first fluid conduit of the debridement tool to the negative-pressure source; and
   a fluid supply conduit adapted to fluidly connect the second fluid conduit of the debridement tool to the fluid source.

8. The system of claim 1, wherein the brush comprises a plurality of bristles, each of the plurality of bristles having a length in a range of 4 mm to 15 mm.

9. The system of claim 1, wherein the brush comprises a plurality of bristles, each of the plurality of bristles having a length in a range of 6 mm to 9 mm.

10. The system of claim 1, wherein the brush comprises a plurality of bristles, each of the plurality of bristles having a length of 9 mm.

11. The system of claim 1, wherein the brush comprises a plurality of bristles, each of the plurality of bristles having a length of 6 mm.

12. The system of claim 1, wherein the brush comprises a plurality of bristles, each of the plurality of bristles having a length in a range of 5 mm to 10 mm.

13. The system of claim 1, wherein:
   the debridement tool further comprises a communications transceiver configured to exchange a wireless signal; and
   the control unit further comprises a communications device configured to exchange the wireless signal with the communications transceiver.

14. The system of claim 13, wherein the wireless signal includes one or more control parameters related to operation of the system.

15. The system of claim 13, wherein the wireless signal includes an instruction for controlling the fluid source.

16. The system of claim 13, wherein the wireless signal includes an instruction for controlling the negative-pressure source.

17. The system of claim 1, further comprising a container fluidly coupled to the negative-pressure source and debridement tool and configured to collect fluids.

18. The system of claim 1, further comprising a pressure sensor configured to monitor pressure at the second end of the debridement tool.

19. The system of claim 18, further comprising:
   a pressure-sensing conduit adapted to fluidly connect the pressure sensor to the debridement tool; and
   wherein the debridement tool comprises a third fluid conduit adapted to be in fluid communication with the second end of the debridement tool and the pressure sensor through the pressure-sensing conduit.

20. The system of claim 1, further comprising a flow sensor configured to monitor a flow rate of a fluid being delivered from the fluid source to the debridement tool.

21. The system of claim 1, wherein the debridement tool further comprises a fourth fluid conduit in parallel fluid communication with a portion of the first fluid conduit, wherein the fourth fluid conduit comprises an oscillation device.

22. The system of claim 21, wherein the oscillation device comprises an offset weight configured to rotate.

23. The system of claim 21, wherein the fourth fluid conduit further comprises at least one filter adapted to block fluids from contacting the oscillation device.

24. The system of claim 19, wherein the debridement tool further comprises a rotary valve configured to selectively fluidly connect the first fluid conduit and the third fluid conduit to prevent fluid communication of the first and third fluid conduits with an environment external to the second end of the debridement tool.

25. The system of claim 24, wherein the rotary valve comprises:
   a first passageway sized and adapted to fluidly connect a first section and second section of the first fluid conduit;
   a second passageway sized and adapted to fluidly connect a first section and second section of the second fluid conduit; and
   a pressure return conduit for fluidly connecting the first fluid conduit and the third fluid conduit.

26. The system of claim 1, wherein the debridement tool further comprises:
   a first tubing connector positioned at the first end of the debridement tool and adapted to fluidly connect the first fluid conduit to a negative-pressure delivery conduit; and
   a second tubing connector positioned at the first end of the debridement tool and adapted to fluidly connect the second fluid conduit to a fluid supply conduit.

27. The system of claim 26, wherein the first tubing connector is further adapted to fluidly connect a third fluid conduit of the debridement tool to a pressure-sensing lumen.

28. The system of claim 1, wherein the debridement tool further comprises a housing formed by injection molding.

29. The system of claim 1, wherein the fluid source comprises a reservoir.

30. The system of claim 1, wherein the fluid source comprises a pump.

\* \* \* \* \*

UNITED STATES PATENT AND TRADEMARK OFFICE
CERTIFICATE OF CORRECTION

PATENT NO. : 11,446,049 B2  
APPLICATION NO. : 16/631794  
DATED : September 20, 2022  
INVENTOR(S) : Christopher Brian Locke Page 1 of 1

It is certified that error appears in the above-identified patent and that said Letters Patent is hereby corrected as shown below:

In the Claims

<u>Column 25</u>
Line 11, In Claim 1, delete "end:" and insert -- end; --, therefor.

Signed and Sealed this  
Ninth Day of April, 2024

Katherine Kelly Vidal  
*Director of the United States Patent and Trademark Office*